US010928398B2

(12) United States Patent
Ely

(10) Patent No.: US 10,928,398 B2
(45) Date of Patent: Feb. 23, 2021

(54) METHOD FOR DOUBLE STAINING COLOCALIZED NUCLEAR-MARKERS IN HISTOLOGICAL LYMPHOID OR BONE MARROW TISSUE SAMPLE

(75) Inventor: Scott A. Ely, Pelham, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 360 days.

(21) Appl. No.: 12/641,240

(22) Filed: Dec. 17, 2009

(65) Prior Publication Data
US 2010/0151447 A1 Jun. 17, 2010

Related U.S. Application Data

(60) Provisional application No. 61/138,422, filed on Dec. 17, 2008.

(51) Int. Cl.
| | |
|---|---|
| *G01N 31/00* | (2006.01) |
| *G01N 33/53* | (2006.01) |
| *G01N 33/58* | (2006.01) |
| *G01N 33/574* | (2006.01) |

(52) U.S. Cl.
CPC ......... *G01N 33/581* (2013.01); *G01N 33/574* (2013.01)

(58) Field of Classification Search
None
See application file for complete search history.

(56) References Cited

U.S. PATENT DOCUMENTS

| 8,603,763 B2 * | 12/2013 | Chen-Kiang .... G01N 33/57484 435/7.23 |
|---|---|---|
| 2004/0241653 A1 * | 12/2004 | Feinstein et al. ................. 435/6 |
| 2007/0140540 A1 | 6/2007 | McLaren et al. |
| 2007/0212736 A1 | 9/2007 | Chen-Kiang et al. |
| 2009/0191573 A1 | 7/2009 | Moulin et al. |

FOREIGN PATENT DOCUMENTS

| WO | WO2014/195730 | * 12/2014 |
|---|---|---|

OTHER PUBLICATIONS

Pituch-Noworolska A. Biological properties and sensitivity to induction therapy of differentiated cells expressing atypical immunophenotype in acute leukemia of children. Folia medica Cracoviensia. 2001; 42(3): 5-80. Abstract Only.*
Compton, et al. Coronavirus Species Specificity: Murine Coronavirus Binds to a Mouse-Specific Epitope on Its Carcinoembryonic Antigen-Related Receptor Glycoprotein. J. Virol. 1992, 66(12):7420.*
Alexandrakis et al., The relation between bone marrow angiogenesis and teh proliferation index Ki-67 in multiple myeloma, 2004, Journal of Clinical Pathology, vol. 57, p. 856-860.*
Hans et al., Confirmation of the molecular classification of diffuse large B-cell lylmphoma by immunohistochemistry using a tissue microarray, 2004, Blood, Vo 103, No. 1, p. 275-282.*
Van Der Loos et al., Practical suggestions for successful immunoenzyme double-staining experiments, 1993, Hisotchemical Journal, vol. 25, p. 1-13, 1993.*
Shin, Chest, vol. 102, p. 946-948, 1992.*
Kremer, Journal of Pathology, vol. 205, p. 92-101, 2005.*
Muro (Journal of Autoimmunity, vol. 10, p. 499-503, 1997).*
Bendig M. M. (Methods: A Companion to Methods in Enzymology, 1995; 8:83-93).*
Paul, Fundamental Immunology, 3rd Edition, 1993, pp. 292-295.*
Rudikoff et al. (Proceedings of the National Academy of Sciences USA, vol. 79, p. 1979-1983, 1982) (Year: 1982).*
Barrie et al., "High-throughput Screening for the Identification of Small-molecule Inhibitors of Retinoblastoma Protein Phosphorylation in Cells," Analytical Biochem. 320:66-74 (2003).
Ito et al., "Cell Proliferation in Childhood Acute Leukemia: Comparison of Ki-67 and Proliferating Cell Nuclear Antigen Immunocytochemical and DNA Flow Cytometric Analysis," Cancer 69:2176-2182 (1992).
Soslow et al., "MIC2, TdT, bcl-2, and CD34 Expression in Paraffin-Embedded High-Grade Lymphoma/Acute Lymphoblastic Leukemia Distinguishes Between Distinct Clinicopathologic Entities," Human Pathol. 28(10):1158-1164 (1997).
Urashima et al., "Interleukin-6 Promotes Multiple Myeloma Cell Growth via Phosphorylation of Retinoblastoma Protein," Blood 88(6):2219-2227 (1996).
Chilosi et al., "CD138/Syndecal-1: A Useful Immunohistochemical Marker of Normal and Neoplastic Plasma Cells on Routine Trephine Bone Marrow Biopsies," Mod. Pathol. 12(12):1101-1106 (1999).
Leibundgut et al., "In Childhood Acute Lymphoblastic Leukemia the Hypophosphorylated Retinoblastoma Protein, p110RB, is Diminished, as Compared with Normal CD34 Peripheral Blood Progenitor Cells," Ped. Res. 45(5, part 1 of 2):692-696 (1999).
Hirt et al., "Site-Specific Phosphorylation of Retinoblastoma Protein Due to Different Cyclin-Dependent Kinase Activities in Childhood Acute Lymphoblastic Leukemia (ALL)," Blood 98(11, part 2):168 (2001) (Abstract only).

(Continued)

*Primary Examiner* — Lisa V Cook
(74) *Attorney, Agent, or Firm* — Troutman Pepper Hamilton Sanders LLP (Rochester)

(57) ABSTRACT

The present invention relates to kits and methods for performing dual-staining immunohistochemistry (IHC) for the detection of specific cell populations in tissue samples containing heterogeneous populations of cells, which can be observed by a light microscope for co-localization of distinct pigments. The method includes providing a tissue sample comprising fixed cells; exposing the sample to first and second ligands that recognize different marker proteins found at the same cellular location, thereby forming a ligand-labeled sample; exposing the ligand-labeled sample to first and second labeling reagents, the first labeling reagent binding to the first ligand and the second labeling reagent binding to the second ligand, the first and second labeling reagents each forming distinct pigments; and identifying the number of cells that display only one particular pigment, or more than one pigment, by the different coloration of the cellular location labeled by the distinct pigment.

25 Claims, 10 Drawing Sheets
(8 of 10 Drawing Sheet(s) Filed in Color)

(56) References Cited

OTHER PUBLICATIONS

Pui et al., "Clinical and Biologic Relevance of Immunologic Marker Studies in Childhood Acute Lymphoblastic Leukemia," Blood 82:343-362 (1993).
Sivamurthy et al., "Attenuated Retinoblastoma Gene Product and Associated E2F/Retinoblastoma Imbalance in Anastomotic Intimal Hyperplasia," J. Vasc. Surgery 35:1233-1241 (2002).
Gondo et al., "HLA Class II Antigen Associated Invariant Chain Gene Expression in Malignant Lymphoma," British J. Haematol. 67:413-417 (1987).
Kaiser, J., "First Pass at Cancer Genome Reveals Complex Landscape," Science 313:1370 (2006).
Montesano et al., "Genetic Alterations in Esophageal Cancer and their Relevance to Etiology and Pathogenesis: A Review," Intl. J. Cancer 69(3):225-235 (1996).
Lees et al., "The Retinoblastoma Protein is Phosphorylated on Multiple Sites by Human cdc2," Embo. J. 10(13):4279-4290 (1991).
Zarkowska et al., "Monoclonal Antibodies Specific for Underphosphorylated Retinoblastoma Protein Identify a Cell Cycle Regulated Phosphorylation Site Targeted by CDKs," Oncogene 14:249-254 (1997).
Stedman's Medical Dictionary 25th Ed. p. 1029-1030 (1990).
Kibel et al., "Loss of Heterozygosity at 12P12-13 in Primary and Metastatic Prostate Adenocarcinoma," J. Urol. 164(1):192-196 (2000).
Dong et al., "Deletion at 13q21 is Associated with Aggressive Prostate Cancers," Cancer Res. 60:3880-3883 (2000).
Zhau, H.E., "Biomarkers Associated with Prostate Cancer Progression," J. Cell Biochem. Suppl. 19:208-216 (1994).
Ren et al., "Reduced Lysyl Oxidase Messenger RNA Levels in Experimental and Human Prostate Cancer," Cancer Res. 58(6):1285-1290 (1998).
Gingrich et al., "Metastatic Prostate Cancer in a Transgenic Mouse," Cancer Res. 56(18):4096-4102 (1996).
Russo et al., "Expression of the Mage Gene Family in Primary and Metastatic Human Breast Cancer: Implications for Tumor Antigen-Specific Immunotherapy," Int. J. Cancer 64:216-221 (1995).
Dalton et al., "Multiple Myeloma," Hematology 1:157-177 (2001).
Klasa et al., "Rational Approached to Design of Therapeutics Targeting Molecular Markers," Hematology 443-462 (2001).
Park et al., "Arsenic Trioxide-Mediated Growth Inhibition in MC/CAR Myeloma Cells via Cell Cycle Arrest in Associate with Induction of Cyclin-Dependent Kinase Inhibitor, p21, and Apoptosis," Cancer Res. 60:3065-3071 (2000).
Park et al., "Monesin-Mediated Growth Inhibition in NCI-H929 Myeloma Cells via Cell Cycle Arrest and Apoptosis," Int. J. Oncol. 23(1):197-204 (2003).
Sherr, C.J., "Cancer Cell Cycles," Science 274:1672-1677 (1996).
Urashima et al., "Interleukin-6 Overcomes p21WAF1 Upregulation and G1 Growth Arrest Induced by Dexamethasone and Interferon-gamma in Multiple Myeloma Cells," Blood 90(1):279-289 (1997).
Kanavaros et al., "Immunohistochemical Expression of the p53, p21/Waf-1, Rb, p16 and Ki67 Proteins in multiple Myeloma," Anticancer Res. 20:4619-4626 (2000).
Levenson et al., "Multispectral Imaging in Biology and Medicine: Slices of Life," Cytomet. A 69A:748-758 (2006).
Madelung et al., "A Novel Immunohistochemical Sequential Multi-Labelling and Erasing Technique Enables Epitope Characterization of Bone Marrow Pericytes in Primary Myelofibrosis," Histopathol. 60:554-560 (2012).
Van der Loos et al., "Accurate Quantitation of Ki67-Positive Proliferating Hepatocytes in Rabbit Liver by a Multicolor Immunohistochemical (IHC) Approach Analyzed with Automated Tissue and Cell Segmentation Software," J. Histochem. Cytochem. 61(1):11-18 (2013).
Van der Loos, "Chromogens in Multiple Immunohistochemical Staining Used for Visual Assessment and Spectral Imaging: the Colorful Future," J. Histotechnol. 33(1):31-40 (2010).
Van der Loos, "Multiple Immunoenzyme Staining: Methods and Visualizations for the Observation with Spectral Imaging," J. Histochem. Cytochem. 56(4):313-328 (2008).

* cited by examiner

Patient 1

FIG. 7A
FIG. 7B
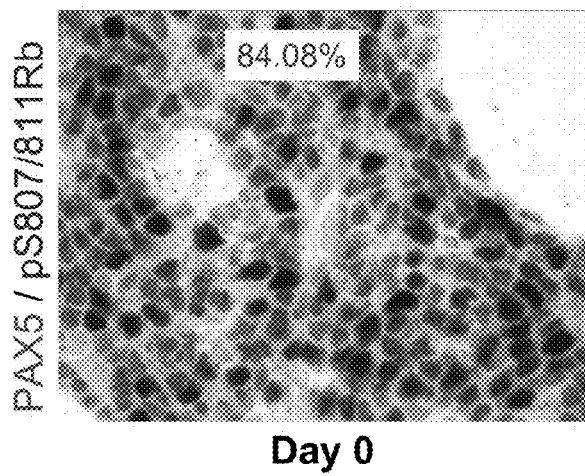
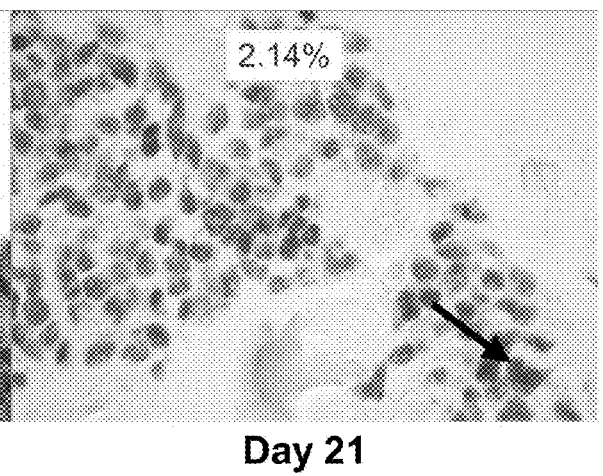
Day 0
Day 21
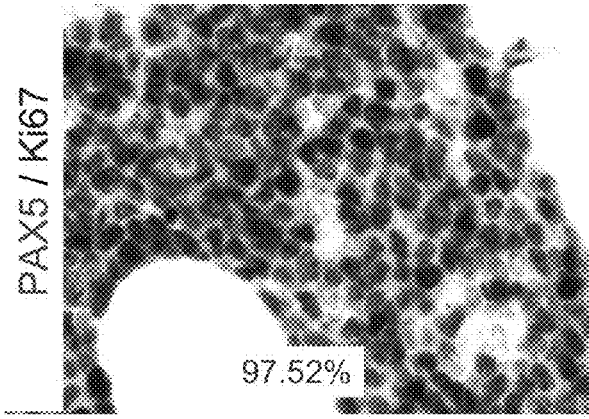
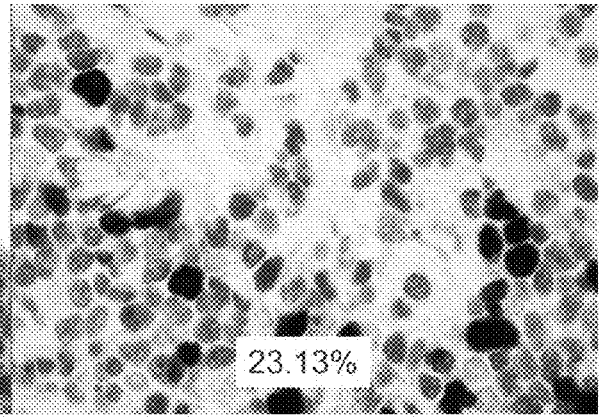
FIG. 7C
FIG. 7D

METHOD FOR DOUBLE STAINING COLOCALIZED NUCLEAR-MARKERS IN HISTOLOGICAL LYMPHOID OR BONE MARROW TISSUE SAMPLE

This application claims the priority benefit of U.S. Provisional Patent Application Ser. No. 61/138,422, filed Dec. 17, 2008, which is hereby incorporated by reference in its entirety.

FIELD OF THE INVENTION

The present invention relates generally to immunohistochemistry ("IHC") methods for functional assessment of specific cell types in fixed tissue samples. More specifically, the invention relates to kits and methods that employ two distinct chromogens that localize to the same cell structure and their resulting pigments can be observed by a light microscope. Co-localization of the pigments can be analyzed manually or by automatic scanning of the tissue section.

BACKGROUND OF THE INVENTION

Traditional methods of detecting gene expression detect or measure protein or RNA extracted from whole tissue. However, the observation of gene expression within specific cell types is critical in many clinical scenarios. For example, in observing or diagnosing bone marrow cancers (e.g. multiple myeloma, lymphoma, or leukemia), it is important to be able to discern in bone marrow samples which cells are cancerous and which of the cancerous cells are expressing a particular protein. Typically, such cancerous cells producing this protein are admixed with large numbers of non-cancerous cells or cancerous cells lacking this protein. For example, if the protein is indicative of cell proliferation, the proportion of cancerous cells that are proliferating provides evidence of the aggressiveness of the cancer or the effectiveness of a therapy being used to treat the cancer. However, non-cancer cells expressing the protein indicative of cell proliferation must be excluded from the analysis; such exclusion is not possible using other methods.

Single cell-level analysis is best performed by co-localization, which allows for the detection of two substances in the same cell. Most co-localization studies are done by immunofluorescence ("IF") microscopy or flow cytometry. Flow cytometry is undesirable because it does not allow for any visualization or morphologic assessment. By IF, two fluorochromes are used, each attached to a ligand that binds to a specific biomarker. For example, to determine whether two different proteins are present in the same subpopulation of cells, the first protein could be detected by a yellow fluorochrome and the second one by a blue fluorochrome; the blue filtered image is then merged with the yellow filtered image; the overlapping green area is evidence of co-localization. However, immunofluorescent microscopy has several major disadvantages. Direct co-localization is not possible by IF; it can only be assessed indirectly by merging separate images of each fluorochrome. IF requires a dedicated dark room facility with fluorescence microscopy equipment. IF is generally restricted to frozen material and thus requires a cryostat microtome for preparation and freezers for specimen storage. Because IF detection signals begin fading within hours, analysis must be performed and archived immediately. For these reasons, most diagnostic or pathology laboratories are not equipped for IF.

Traditionally, IHC techniques have been widely used for observing cellular content. IHC is performed on routinely preserved, paraffin-embedded (not frozen) tissue using standard light microscopy. IHC slides can be archived and re-analyzed, even up to decades later. For these reasons, IHC is the diagnostic standard widely used in pathology laboratories and industry, whereas IF use is limited to the research setting and, even there, its use is rapidly waning.

To date, however, it has been impossible to do light microscopy IHC co-localization studies where the biomarkers under investigation are both located in the same cellular compartment. That is because the chromophores (or stains) typically used, like diaminobenzidine ("DAB"), are opaque or overpowering, so that co-localization is masked or undetectable. More importantly, the ability to do co-localization studies with light microscopy would enable studies with new markers on routinely preserved specimens as well as computer image analysis. Enabling co-localization on paraffin embedded tissue by IHC and light microscopy would likely lead to widespread use and a new standard for sample analyses.

The present invention is directed to overcoming these and other deficiencies in the art.

SUMMARY OF THE INVENTION

A first aspect of the invention relates to a method for IHC analysis of specific cell populations in tissue samples containing heterogeneous populations of cells. The method includes: providing a tissue sample that includes fixed cells; exposing the tissue sample to first and second ligands that recognize different marker proteins found at the same cellular location, thereby forming a ligand-labeled sample; exposing the ligand-labeled sample to first and second labeling reagents, the first labeling reagent binding to the first ligand and the second labeling reagent binding to the second ligand, the first and second labeling reagents each forming distinct pigments; and identifying the number of cells that display only one particular pigment, or more than one pigment, by the different coloration of the cellular location labeled by the distinct pigments.

A second aspect of the present invention relates to a method of detecting proliferating cancerous cells in a tissue sample by performing the method according to the first aspect of the invention, wherein the first ligand binds to a nuclear marker protein for a cancer cell and the second ligand binds to a nuclear cell cycle marker protein, and proliferating cancerous cells are identified by the presence of a nucleus stained by both pigments.

A third aspect of the present invention relates to a method of assessing the cancer status and progression in a tissue sample. This method includes performing the method according to the first aspect of the invention where at least one of the marker proteins is specific for a cancer cell, and the method is performed on at least two occasions with a time delay between the at least two occasions; and determining whether there exists, following the time delay, an increase in the percentage of cells in the patient sample that are identified during said identifying step, wherein the increase indicates a resurgence or progression of the cancerous condition.

A fourth aspect of the present invention relates to a method of assessing the efficacy of cancer therapy by performing the method according to the first aspect of the invention where at least one of the marker proteins is specific for a cancer cell, and the method is performed on first and second patient samples obtained from a cancerous tissue of a patient before and after, respectively, providing cancer therapy to the patient, wherein a change (decrease) in the percentage of identified cells indicates the efficacy of the cancer therapy.

A fifth aspect of the present invention relates to a method of detecting cells infected by viruses in a tissue sample by performing the method according to the first aspect of the invention, wherein one ligand recognizes a nuclear marker protein for a specific cell type susceptible to virus infection and the other ligand recognizes one or more viral molecules selected from the group of viral protein, mRNA, or DNA; and wherein the identifying step includes identifying the number of susceptible cells that display co-localization of more than one pigment.

A sixth aspect of the present invention relates to a method of detecting cells undergoing apoptosis in a tissue sample by performing the method according to the first aspect of the invention, wherein one ligand recognizes a nuclear marker protein for a specific cell type and the other ligand recognizes a nuclear protein marker for apoptosis; and wherein the identifying step includes identifying the number of cells that display co-localization of more than one pigment.

A seventh aspect of the present invention relates to a kit that includes: a first ligand that recognizes a marker protein found at a specific cellular location; a second ligand that recognizes a marker protein found at the specific cellular location; a first labeling reagent that binds specifically to the first ligand, the first labeling reagent, when exposed to a first chromogen, forms a first pigment having a color; and a second labeling reagent that binds specifically to the second ligand, the second labeling reagent, when exposed to a second chromogen, forms a second pigment having a color that is distinct of the color of the first pigment and, upon co-localization with the first pigment, the two pigments generate a distinct, intermediate color.

An eighth aspect of the present invention relates to a method of analyzing an image of an immunohistochemistry sample that includes at least two pigments, which may be co-localized at a cellular structure. This method includes the steps of: providing an image of an immunohistochemistry sample containing at least two pigments; determining whether a stained cellular structure satisfies a set of predetermined criteria for the cellular structure; and determining whether the stained cellular structure that satisfies the set of predetermined criteria satisfies color criteria for the first pigment, the second pigment, or the presence of both pigments.

A ninth aspect of the present invention relates to a computer readable medium that includes a program of instructions executable by a machine (containing a processor) to perform the method steps according to the eighth aspect of the present invention.

This invention provides a method for double staining tissue samples, e.g., using methods typical of IHC but employing two different chromogens, each producing a distinctly colored product, and which when co-localized those products form a distinct color that is different than either isolated color. These differences in color are detectable by naked eye and are measurably different by computer scanning. While some light reactive IHC co-localization studies have been successful in showing two proteins in the same cell (e.g., one protein in the nucleus and another in the cell membrane), none have shown co-localization in the same cellular structure as in the present invention. In the present invention, the two labeling reagent systems allow for co-localization studies in the same cell structure to be viewed by routine light microscopy. As demonstrated in the Examples, this type of co-localization makes automated image analysis possible, since the parameters of the single cell compartment (or whole cell) to be detected and the spectral properties of the variously colored products can be readily characterized. The Examples demonstrate the detection of variously labeled nuclei and cell membranes, which has allowed for diagnosis of cancerous conditions as well as assessment of cancer therapy efficacy, and, more broadly, the measurement of an immune response in antigen-exposed tissue.

BRIEF DESCRIPTION OF THE DRAWINGS

The patent or application file contains at least one drawing executed in color. Copies of this patent or patent application publication with color drawings will be provided by the office upon request and payment of the necessary fee.

FIG. 1A illustrates the immunohistochemistry method, and FIG. 1B illustrates a process for automated scoring of labeled cells or cell structures in the images obtained using light microscopy.

FIG. 3A shows the raw image. FIG. 3B illustrates the same image following automated assessment for cycling MM cells as a percentage of all MM cells, by computing the number of purple nuclei, as a percentage of red (non-cycling MM cells) plus purple (cycling MM cells). The scanned images of the dual stained slides are assessed by an algorithm that involves applying predetermined parameters (such as nuclear size, axis-ratio shape, and color). In this example, the software counts a cell as MM-non-cycling (asterisks) or cycling-MM (dot). The algorithm can be adjusted by the user to increase or decrease specificity. In this sample, cells that are neither sufficiently red nor sufficiently purple are not included, and cells that are too large, too small, or oddly shaped also are not included. Lastly, if desired, the user can also assess cycling non-MM cells (blue nuclei).

FIGS. 7A-D are images of histological lymph node sections from a B cell lymphoma patient as observed under a light microscope. In FIGS. 7A-D, the nuclear protein PAX5, a biomarker for B cells, has been stained with a specific chromogen affording a red pigment (Bond™ Polymer AP Red Detection System, DS9305, Leica, Bannockburn, Ill.). In FIGS. 7A-B only, serine-phosphorylated retinoblastoma protein (pS-Rb) has been stained with a specific chromogen affording a blue pigment (Blue Alkaline Phosphate Substrate Kit produced by Vector Laboratories, Burlingame, Calif.). In FIGS. 7C-D only, Ki67 (bottom row) has been stained with the same chromogen affording a blue pigment. Each staining system was used on samples taken before and after 21 days of therapy with the CDk4/6 inhibitor. By image analysis, Rb phosphorylation by Cdk4/6 at serine 807/811 ($pS^{807/811}Rb$) was found in 84.08% of lymphoma cells before treatment but was reduced successfully to only 2.14% by day 21 of therapy (arrow at right indicates $pS^{807/811}Rb^+$ lymphoma cell, purple nucleus, in a group of negative lymphoma cells, red nuclei) (see FIGS. 7A-B). There was also a drop in Ki67 expression, from 97.52% of lymphoma cells prior to treatment, to 23.13% on day 21 (see FIGS. 7C-D). A response of this magnitude signals that this specific patient is responding to this specific drug, as assessed at the single cell level in the patient's tissue biopsy. The clinician may use this data to decide whether or not to keep the patient on the trial.

(PAX5(neg)/p18(neg), colorless areas). By contrast, the mantle zone contains mainly PAX5+/p18(neg) B cells (red). The germinal center, however, contains mainly PAX5+/p18+ B cells (purple). This confirms published data, showing the role of p18 in B cell maturation to the fully mature plasma cell stage (Tourigny et al., "CDK Inhibitor p18 (INK4c) Is Required for the Generation of Functional Plasma Cells," *Immunity* 17:179-189 (2002), which is hereby incorporated by reference in its entirety).

DETAILED DESCRIPTION OF THE INVENTION

The invention relates generally to methods for IHC analysis of specific cell populations in tissue samples containing heterogeneous populations of cells, kits for practicing the IHC methods, and methods and systems for analyzing the prepared IHC samples.

Figure 1A:
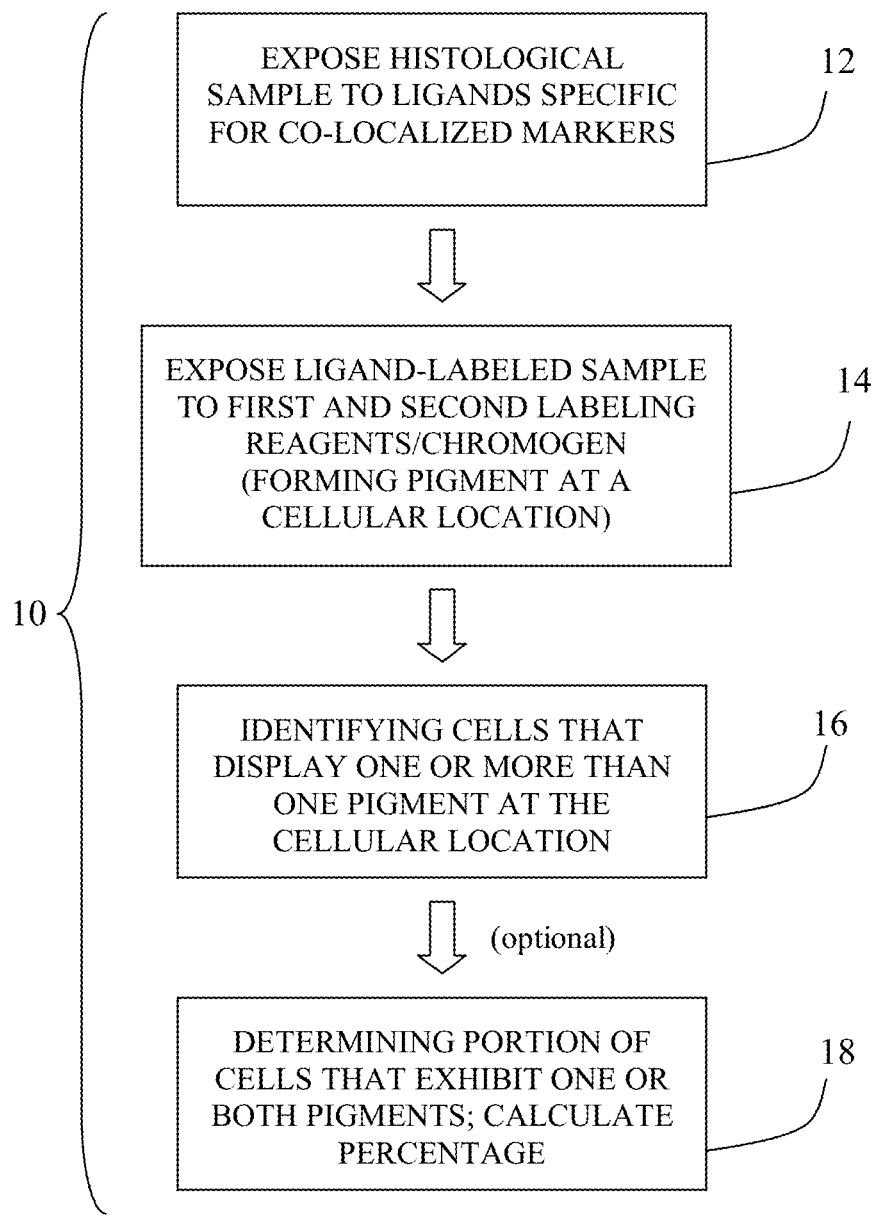
FIGS. 1A-B are flow diagrams illustrating a method for double-staining immunohistochemistry in accordance with one embodiment of invention.

With reference to FIG. 1A, according to one aspect of the invention a method for IHC analysis of specific cell populations in tissue samples containing heterogeneous populations of cells is generally denoted by reference numeral 10. The method includes providing a tissue sample comprising fixed cells; exposing the sample to first and second ligands (step 12) that recognize different marker proteins found at the same cellular location, thereby forming a ligand-labeled sample; and then exposing the ligand-labeled sample to first and second labeling reagents (step 14) that bind, respectively, to the first and second ligands. Upon exposure of the first and second labeling reagents to first and second chromogen, respectively, these reagents form distinct pigments. The method further includes identifying the number of cells that display only one particular pigment, or more than one pigment, by the different coloration of the cellular location labeled by the pigment(s) (step 16). Rinsing steps may be employed after steps 12 and 14 to avoid non-specific binding of the ligand or labeling reagents. In addition, prior to step 16, the pigment may be deposited at the cellular location of the ligand in accordance the appropriate chromogenic system that is employed (discussed infra).

The analysis of the specific cell populations may optionally include a step of determining the portion of cells of that exhibit one or both pigments (step 18). For example, one calculation may involve assessing the portion of cells that display both pigments relative to the sum of those that display both pigments and those that display only one of the pigments. Alternatively, another calculation may involve assessing the portion of cells that display only one pigment relative to the sum of those that display both pigments and those that display only the one pigment.

The methods of the invention are intended to be performed on samples that contain fixed cells. The sample can be any sample suitable for pathological examination, which has been fixed using an appropriate fixative. Exemplary fixatives include, without limitation, formalin and Bouin's solution, and the use thereof is well known in the art. The fixed sample is typically embedded in an embedding media such as paraffin or resin. The sample to be used in carrying out the methods of the present invention may be cut into sections and mounted on slides that are suitable for microscopic examination, e.g., glass or plastic slides. No deviation from the standard protocol for pathology specimen handling is required to prepare the samples for analysis. Suitable specimens include, without limitation, tissue samples or biopsies, organ resections, and fluid samples.

The tissue sample can be any sample that contains cells of interest, in which case the sample can be a fluid sample or a solid tissue sample. Although the invention is not limited to cancer cell detection, that is one suitable utility thereof. Thus, tissue specimen can include specimens of solid tumors found in all non-hematopoietic sites, including, but not limited to lung, breast, colon and entire gastrointestinal tract, prostate, brain, pancreas, and skin. The tissue specimen can also include non-solid tumors, e.g., lymphomas, leukemias, and plasma cell neoplasms, and involves the analysis of patient tissues that include all hematopoietic organs, without limitation, blood, lymph nodes, tonsil, spleen, thymus, and bone marrow.

As used herein, the term "marker protein of interest" refers to any protein that is intended to be identified in accordance with the double IHC methods of the present invention. The marker protein of interest is objectively measured and evaluated as an indicator of normal biologic or pathogenic processes, or pharmacologic responses to a therapeutic intervention.

As used herein, the term "ligand" refers to any agent that is capable of specifically binding to, i.e., recognizing, a marker protein of interest. Exemplary ligands include nucleic acid molecules and proteins or polypeptides that have a high degree of affinity and specificity for the marker protein of interest. Suitable nucleic acid molecules include, without limitation, RNA and DNA aptamers, which may also include an affinity label. Suitable proteins and polypeptides include, without limitation, antibodies and antibody fragments, as well as antibody mimics.

Suitable antibodies are preferably monoclonal antibodies, but may also include mono-specific polyclonal antiserum. Suitable antibody fragments include, without limitation, Fab fragments, F(ab)$_2$ fragments, Fab' fragments, F(ab')$_2$ fragments, Fd fragments, Fd' fragments, Fv fragments, 61-residue subdomains of the antibody heavy-chain variable domain known as minibodies (Pessi et al., "A Designed Metal-binding Protein with a Novel Fold," *Nature* 362:367-369 (1993), which is hereby incorporated by reference in its entirety), and domain antibodies (dAbs) (Holt et al., "Domain Antibodies: Proteins for Therapy," *Trends Biotechnol.* 21:484-90 (2003), which is hereby incorporated by reference in its entirety). Many of these antibody fragments can be made by conventional procedures, such as proteolytic fragmentation procedures, as described in J. Goding, MONOCLONAL ANTIBODIES: PRINCIPLES AND PRACTICE 98-118 (1984), which is hereby incorporated by reference in its entirety.

Suitable antibody mimics include, without limitation, those known as monobodies, which are derived from the tenth human fibronectin type III domain (Koide et al., "The Fibronectin Type III Domain as a Scaffold for Novel Binding Proteins," *J. Mol. Biol.* 284:1141-1151 (1998); Koide et al., "Probing Protein Conformational Changes in Living Cells by Using Designer Binding Proteins: Application to the Estrogen Receptor," *Proc. Nat'l Acad. Sci. USA* 99:1253-1258 (2002), each of which is hereby incorporated by reference in its entirety); and those known as affibodies, which are derived from the stable α-helical bacterial receptor domain Z of staphylococcal protein A (Nord et al., "Binding Proteins Selected from Combinatorial Libraries of an α-Helical Bacterial Receptor Domain," *Nat. Biotechnol.* 15(8):772-777 (1997), which is hereby incorporated by reference in its entirety). Variations in these antibody mimics can be created by substituting one or more domains of these polypeptides and then screening the modified monobodies or affibodies for specificity for binding to marker proteins of interest.

The marker proteins of interest, which are to be identified in accordance with the present invention, are located at the same cellular location. In other words, the marker proteins of interest are both located on or in a specific component of a cell. The marker proteins of interest need not be in direct contact or in immediate proximity to one another, but rather under light microscopy at appropriate magnification appear to co-locate at or in the specific cell component of interest. The level of magnification should be suitable to discern whether or not the pigments co-locate. Exemplary cell components where the marker proteins of interest can reside include any cellular organelle or region, including the nucleus, nuclear membrane, cytoplasmic membrane, mitochondria, Golgi and endoplasmic recticulum. As should be appreciated by persons of skill in the art, the specific marker proteins of interest will depend upon the nature of inquiry that is being performed.

The term "labeling reagent" refers to a type of reagent that binds specifically to the ligand. According to one embodiment, this reagent is a secondary antibody, antibody fragment, or antibody mimic that binds specifically to the ligand. According to one embodiment, the labeling reagent also includes a dye or pigment tethered thereto such that the dye or pigment will directly label the location of the ligand. According to another embodiment, the reagent includes an enzyme that is capable of converting a chromogen into a pigment or dye. (A chromogen that is converted to a pigment by an enzyme is known as a chromogenic substrate.) The use of an enzyme as a component of the labeling reagent is often desirable, because a single enzyme can catalyze the reaction of multiple chromogenic substrate molecules, which amplifies the amount of colored product formed at the site of the ligand. Regardless of the specific labeling approach, the pigment or dye is used indirectly to label the cellular location of the ligand (bound to the marker protein of interest).

Any plurality of compatible chromogen can be employed in the present invention as long as the chromogen yield pigments of distinct but inherently mergeable colors. This means that each chromogen affords a pigment having a distinct color, but when co-localized the pigments together yield a distinctive intermediate color that is viewable or detectable in a single image. (This is not to be confused with two differently labeled images that are themselves merged, as is commonly performed using IF techniques.) By way of example, one chromogen may afford a pigment having a red color, the other chromogen may afford a pigment having a blue color, and when co-localized the two pigments yield an intermediate purple color. The use of the plurality of chromogen is intended to be carried out in the absence of background staining or contrasting stains that might interfere with observation or detection of the pigments.

Two preferred chromogen which are compatible include those afforded by the Bond™ Polymer AP Red Detection System (DS9305, Leica, Bannockburn, Ill.), affording a red pigment, and the Blue Alkaline Phosphate Substrate Kit (Vector Laboratories, Burlingame, Calif.), affording a blue pigment. Both of these systems utilize an alkaline phosphatase enzyme as a component of the labeling reagent, and a chromogenic substrate to generate the corresponding red or blue pigments, respectively. Use of these two chromogen is illustrated in the accompanying Examples.

Without being limited by the mechanism involved, it is believed that while most chromogenic precipitates (pigments) are totally insoluble under the conditions observed under light microscopy, the two preferred labeling reagents/chromogens identified in the preceding paragraph form products that display some limited solubility on the outer layer of the precipitate, which allows their individual spectral properties to merge. Hence, it is expected that any other chromogenic precipitates that share such solubility properties will be useful in the co-localization detection processes of the present invention. Despite the possibility of this limited solubility, the resulting precipitate (pigment or dye) remains at the site of the labeled antigen. Moreover, it is also possible that the polymeric system of the secondary (antibody) labeling reagent used to identify the ligand in the Examples provides a phase in which the two pigments are soluble but stationary at the overlapping antigenic sites.

The use of compatible chromogen in accordance with the present invention is distinct of pigments typically used for light microscopy, diaminobenzidine (DAB), which has a dark brown color that would mask or interfere with detection of other chromogens. For this reason, use of DAB should be avoided in the present invention.

Having exposed the sample to ligand and labeling reagent, and generated pigments at the site of the ligand (and its bound marker protein), the resulting images obtained using light microscopy can be analyzed to identify the results of the labeling procedures (i.e., step 16 of FIG. 1A). While the labeling of cells or cell structures with the co-localized pigments can be carried out manually by counting the cells or cell structures (i.e., within a field of view or captured image) that are labeled by the first or second pigments, or both, counting may also be performed using an automated scoring system.

Any suitable automated scoring system can be used in scoring the images obtained using the present invention. According to one embodiment, the automated scoring system is based on the Ariol™ image analysis system (Applied Imaging, San Jose, Calif.).

Figure 1B:
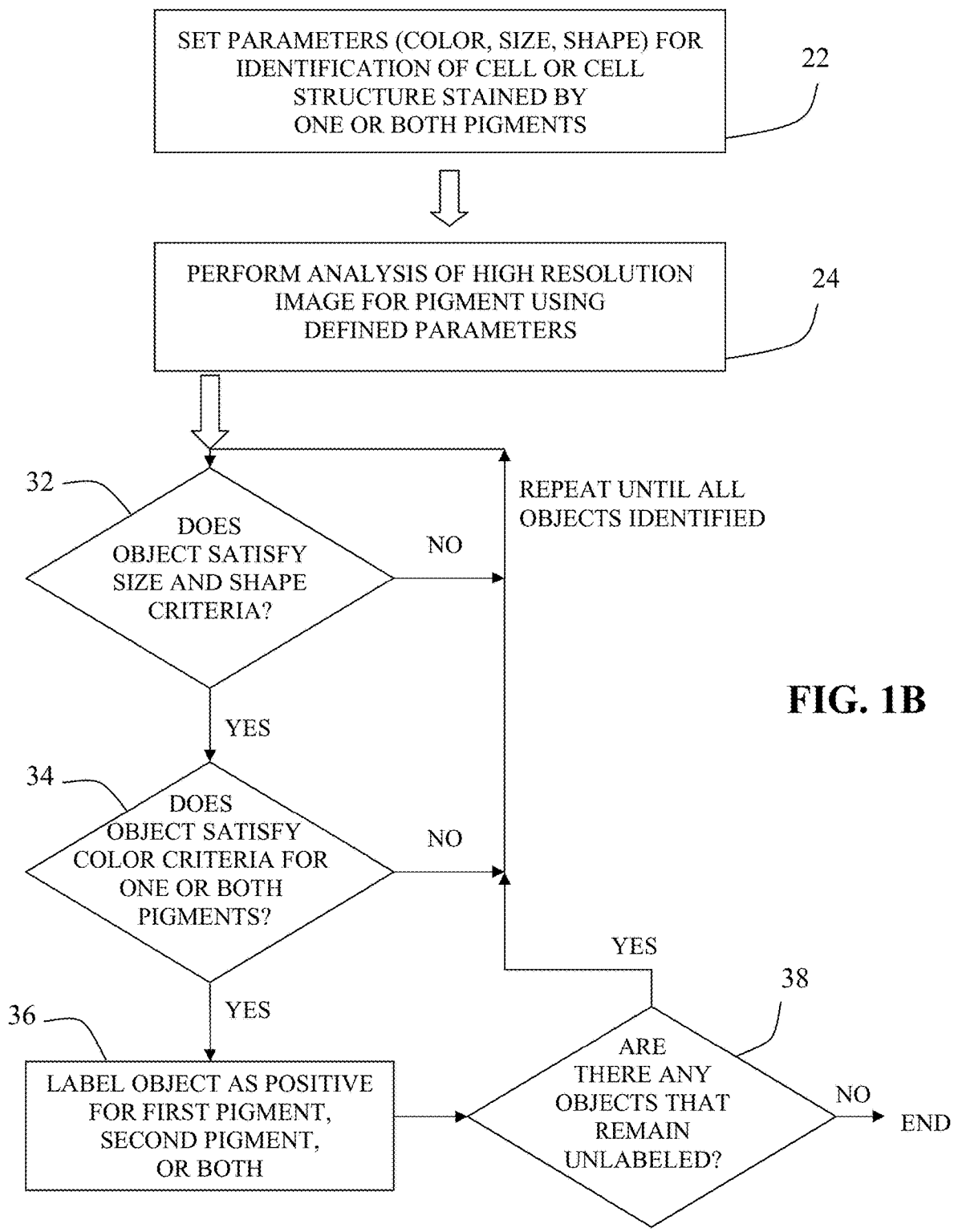

Referring to FIG. 1B, the automated scoring system is used to carry out step 16 by first training the system at step 22 to set the parameters of detection and then at step 24 to execute the analysis using the defined parameters. The parameters can include the size, shape, and aspect ratio of the object (that is stained) as well as the color and intensity of staining that is observed. For example, for detection of a cellular structure such as the nucleus it is possible to identify the size, shape, and aspect ratio parameters (i.e., upper and lower limits) for the nucleus. If a stained object meets the criteria of these parameters (at step 32), then it is deemed to be a nucleus. (If not, the query is repeated for another stained structure.) The identified nucleus is then assessed to determine whether it satisfies the color criteria for the first pigment, the second pigment, or the presence of both pigments (at step 34). If the nucleus is stained with the first pigment it can be labeled one way, and if it is stained with both pigments it can be labeled another way (step 36) (see, e.g., FIG. 3B). Alternatively, if the nucleus is stained only with the second pigment it can be labeled yet another way. Regardless of the labeling process that is employed, the entire field being analyzed can be screened in this manner until no further stained nuclei remain unlabeled (step 38). As an alternative to the process outlined above, the color parameters can be used first, followed by use of the size, shape, and aspect ratio parameters. Once the entire field of interest has been labeled, any desired calculations can be performed as discussed above.

Similar processes can be carried out for other cellular structures or for cellular membranes. Each different cellular structure will have different size, shape, and aspect ratio parameters. The color parameters will depend, of course, on the particular choice of pigments being employed.

As an alternative to training the image analysis system, the parameters can be provided in the form of a computer readable medium that includes a plurality of lookup tables that identify the parameters for particular cell types or cell structures, and color parameters for pigments/chromogenic systems, and process commands, which when executed by a computer or other machine containing a processor for carrying out those commands will allow for the automated analysis and labeling of the images.

According to one embodiment, the double-staining IHC methods of the present invention can be employed for the detection or monitoring of cancerous conditions, as well as the monitoring of treatment efficacy.

The cancer condition (or therapy) to be diagnosed or screened in accordance with the present invention can be any solid tumor or leukemia. However, the present invention is particularly adept at screening hematopoietic cancers where the cancer cells are present in a mixed population of cells. Exemplary hematopoietic cancers include, without limitation, all acute myelogenous leukemias (AML); acute promyelocytic leukemia (APL); all myeloproliferative disorders (MPD), including chronic myelogenous leukemia (CML), polycythemia vera, essential thrombocythemia, and idiopathic myelofibrosis; all myelodysplastic syndromes (MDS) and myelodysplastic/myelo-proliferative diseases; all acute lymphoblastic leukemias (ALL), including precursor B-lymphoblastic leukemia/lymphoma and precursor T lymphoblastic leukemia/lymphoma; chronic lymphocytic leukemia (CCL); multiple myeloma (MM); monoclonal gammopathy of undetermined significance (MGUS); amyloidosis; Hodgkin lymphoma (HL), including all classical Hodgkin lymphoma cell types (e.g., Reed Sternberg cell; including nodular sclerosis, mixed cellularity and lymphocyte depleted types); all non-Hodgkin's lymphomas (NHL) including all B cell, all T cell and all NK cell types; histiocytic disorders; and mastocytosis.

According to one approach, the double-staining IHC method of the present invention can be used to detect the number of bone marrow cancer cells that have entered the cell cycle (FIG. 2) and have, therefore, begun to proliferate. This information helps in determining when a hematopoietic cancer patient is about to progress and needs treatment. For example, multiple myeloma cells cycle infrequently except during relapse, in which cell replication can be detected in as high as 100% of the cells. The inability to control cell expansion during relapse is usually the cause of death. Table 1 below lists a number of proteins that are involved in the cell cycle and commercial sources of antibodies to them. The cell cycle proteins pS-Rb (serine-phosphorylated retinoblastoma protein), cyclin D1 and Ki67 are expressed in mid G1 to S, early G1, and S through M, respectively; these markers can be used to determine what phase of the cell cycle the cells positive for these markers are in. Since Ki67 has a longer half-life than other cell cycle proteins, it is often a better marker of cycling cells than pS-Rb (i.e. it is typically present in a greater percentage of cells). Cyclin D1 is a useful marker for some hematopoietic cancers, because non-neoplastic B cells and plasma cells never express cyclin D1. When it is detected in B cells, it is diagnostic of neoplasia; overexpression is generally due to a chromosomal translocation or an increase in chromosome 11 copy number (the locus of the cyclin D1 gene) that leads to its constitutive expression.

TABLE 1

Cell Cycle Regulators/Markers and Antibody Sources

| Protein Recognized | Source |
|---|---|
| Positive CC Regulators | |
| cyclin D1 | Lab Vision Corporation (Fremont, CA) |
| | Novocastra (Peterborough, UK) |
| cyclin D2 | Santa Cruz (Santa Cruz, CA) |
| | Novocastra (Peterborough, UK) |
| cyclin D3 | Novocastra (Peterborough, UK) |
| cyclin E | Novocastra (Peterborough, UK) |
| cdk4 | Cell Signaling Technology Inc. (Beverly, MA) |
| cdk6 | Cell Signaling Technology Inc. (Beverly, MA) |
| Negative CC Regulators | |
| p16 | Novocastra (Peterborough, UK) |
| p18 | Santa Cruz (Santa Cruz, CA) |
| P19 | Novocastra (Peterborough, UK) |
| p21 | Becton-Dickinson (San Jose, CA) |
| p27 | Becton-Dickinson (San Jose, CA) |
| Cell Cycle Marker Proteins | |
| mcm2 | Lab Vision (Fremont, CA) |
| mcm7 | Lab Vision (Fremont, CA) |
| Skp-2 | Zymed (South San Francisco, CA) |
| Ki-67 | Zymed (South San Francisco, CA) |
| phospho-Rb | Cell Signaling Technology Inc (Beverly, MA) |

When employing an antibody to a cell cycle marker protein, that marker is often (though not always) unable to distinguish between normal cycling cells and cancerous cells. In such a case, a second ligand can be used to distinguish between them. Table 2 lists antibodies for nuclear proteins that are unique to specific cancer cells. Thus, double-staining for a cell-cycle protein and a protein specific for a given hematopoietic or other cancer identifies the portion of those cancerous cells that co-express the CC protein of interest.

TABLE 2

Cancer Cell-Specific Nuclear Markers

| Nuclear Protein | Cancer | Source |
|---|---|---|
| MUM1 | Multiple myeloma | Dako (Carpinteria, CA) |
| PAX 5 | lymphoma | BD Biosciences (San Jose, CA) |
| bcl-6 | post-germinal center B cell lymphomas | Santa Cruz (Santa Cruz, CA) |
| TdT (terminal deoxynucleotidyl transferase), | precursor B cell lymphoma/leukemia | BD Biosciences (San Jose, CA) |
| TTF1 (thyroid transcription factor) | thyroid and lung epithelium and cancers | Abcam (Cambridge, MA) |
| neuN | primary brain tumors | Abcam (Cambridge, MA) |
| ER (estrogen receptor) | breast carcinoma | Leica (Bannockburn, IL) |

Figure 3A:
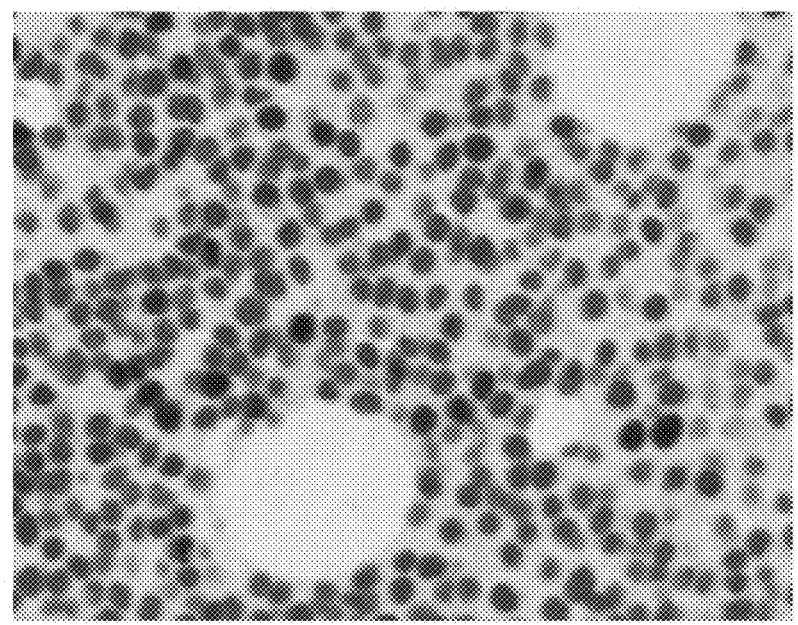
FIGS. 3A-B are images of a histological bone marrow section from a multiple myeloma (MM) patient observed under a light microscope. In the imaged sample, the nuclear protein MUM1, a biomarker for MM cells, has been stained with a specific chromogen affording a red pigment (Bond™ Polymer AP Red Detection System, DS9305, Leica, Bannockburn, Ill.). In addition, the nuclear retinoblastoma protein that has been phosphorylated on a serine residue (pS-Rb), which is a biomarker of progression past the mid-G1 cell cycle check point in all cells, has been stained with a certain chromogen affording a blue pigment (Vector® Blue Alkaline Phosphate Substrate Kit produced by Vector Laboratories, Burlingame, Calif.; hereinafter "Blue Alkaline Phosphate Substrate Kit"). Cells exhibiting red nuclei are non-cycling MM cells. Cells with blue nuclei are non-MM hematopoietic marrow cells that are cycling, i.e., have started to proliferate. Cells with purple nuclei show co-localization of the two markers and represent MM cells cycling past the mid-G1 cell cycle checkpoint. Because no nuclear counterstain is used, cells that are neither in the MM population nor past the mid-G1 checkpoint are invisible.
Figure 3B:
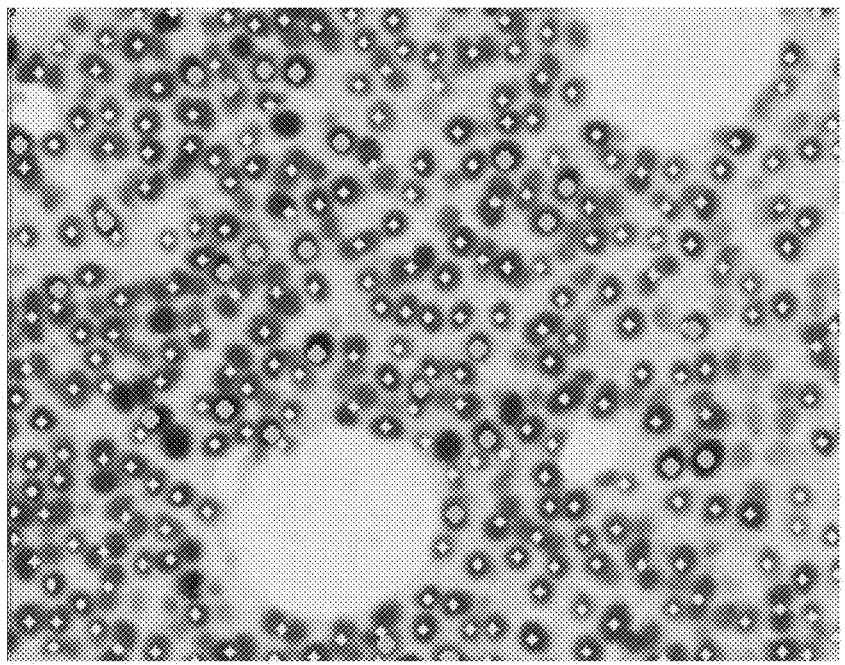

For one approach in assessing hematopoietic cancers, each of the two stains is localized with a ligand that binds to a specific nuclear protein. As demonstrated in the accompanying Examples, MUM1 IHC was used to detect multiple myeloma cells and PAX5 IHC was used to detect lymphoma cells; and these antigens were co-localized with antibodies to Ki67 or pS-Rb to determine the fraction of neoplastic cell populations that are proliferating. FIGS. 3A-B show the results of this double IHC when the anti-MUM1 antibody is stained with a chromogen affording a red pigment (Bond™ Polymer AP Red Detection System, DS9305, Leica, Bannockburn, Ill.); and the anti-pSRb antibody is stained with a chromogen affording a blue pigment (Blue Alkaline Phosphate Substrate Kit produced by Vector Laboratories, Burlingame Calif.). This method detects double staining of MUM1 and pS-Rb or Ki67 in fixed, paraffin embedded patient specimen, and therefore allows for longitudinal studies of samples taken at different times of the disease of each patient and a construction of the history of loss of cell cycle control. This data allows prediction of the rate of increase (or decrease) of tumor load.

Cyclin D1 is another protein that is expressed during the proliferative phase of the cell-cycle, in the early G1 phase. Because cyclin D1 is not expressed in any non-neoplastic B cells or plasma cells, it is a useful second stain for detecting lymphoma or MM cells that are proliferating. Hence, upon double staining for cyclin D1 (blue) and Pax 5 (red), finding any purple cells is diagnostic of lymphoma and would detect 100% of mantle cell lymphoma cells. Likewise, double staining for MUM1 (red) and cyclin D1 (blue) is diagnostic of a plasma cell neoplasm and would detect ~25% of MGUS or MM cases for initial diagnosis and 100% for relapse (in a case already demonstrated to be positive for D1). Double-staining with cyclin D1 could be a very useful tool for minimal residual disease detection.

The double-staining IHC methods of the present invention can be used as a prognostic indicator in myeloma and other cancers. This invention can detect loss of cell cycle control at the single cell level, which will be well in advance of the expansion of cell division and tumor expansion. In the case of multiple myeloma, it is useful to predict disease progression from the early smoldering stage to frank myeloma, and from remission to relapse, and to predict which patients should benefit from treatment and which likely will not. The ability to treat a patient while she is relatively healthy, prior to the consequences of disease advancement, should result in less morbidity and better disease specific survival.

The double-staining IHC methods of the present invention can be used to monitor the treatment outcome in cancers. Myeloma is invariably fatal. Even the most promising drugs such as the proteasome inhibitor PS-341(bortezomib) elicits responsiveness in only 30% of patients. The development of more effective treatment requires improved monitoring of treatment outcome. Detection of an increase in the percentage of multiple myeloma or lymphoma cells that are proliferating will indicate that the treatment protocol used is losing its effectiveness, and will allow for modification of the protocol or selection of a new protocol at an earlier stage of disease progression. More efficient monitoring of treatment outcome should allow for more effective treatment of these cancers.

In addition to the foregoing, it should also be appreciated that the double-staining IHC methods of the present invention can also be used to screen biopsy samples for evidence of metastases from a primary solid tumor. This, too, would involve the detection of cancer cells in a mixed population of cells.

Another use of the double-staining IHC methods of the present invention involve monitoring the treatment of autoimmunity diseases or disorders. Because autoimmunity involves the abnormal expansion of certain immune subpopulations, the invention should be helpful to monitor expansion of specific subpopulations, while excluding others from the assay. This method would allow monitoring through the detection of nuclear protein markers of lymphoid and other immune subpopulations detected together with cell cycle regulator proteins. It can be used as a rapid assay to determine the contribution of loss of cell cycle control in specific cell populations to the progression of autoimmunity disorders.

Another use of the double-staining IHC methods of the present invention includes the detection of viral infections in tissue samples. Viral infections are hard to detect during the incubation period when no symptoms are presented. Also, a carrier of a virus can feel perfectly healthy and be totally unaware of having contracted a viral infection during the latent period of disease. The methods of the present invention can be used to detect viral infection by selecting a pair of ligands, one of them recognizing a specific cell population susceptible to infection and the other recognizing a viral nuclear particle (e.g., DNA, RNA, protein). The presence of cells stained by both pigments (i.e., co-localized) will indicate the occurrence of viral infection. Exemplary viruses that can be identified include, without limitation, HSV 1 and HSV 2 (herpes simplex virus), HIV, CMV (cytomegalovirus), EB (Epstein Barr Virus), Kaposi's Sarcoma Herpes Virus, HPV (Human papillomavirus), HB (Hepatitis B virus), parvovirus B19, and BK virus.

Another use of the double-staining IHC methods of the present invention includes the detection of apoptosis in individual cells of a tissue sample containing a mixed population of cells. The methods of the present invention can be used to detect cells undergoing apoptosis by selecting a pair of ligands, one of them recognizing a nuclear biomarker found in a specific cell type, and the other recognizing a nuclear biomarker indicative of apoptosis (e.g., cleaved caspase 3, cleaved PARP (poly-ADP-ribose-polymerase), Bcl-x, and p53). Apoptotic cells can be quantified by counting the number of cells that are positively stained for both markers.

Another use of the double-staining IHC methods of the present invention includes the in vitro screening of therapeutic agents. The efficacy of certain therapeutic agents can be screened by exposing cell culture samples, developed from the bone marrow of patients needing treatment, to one or more drugs to be screened and then analyzing these samples for the portion of cells of the cancer type being studied that are proliferating by the methods of this invention. A comparison of the untreated cell culture with the treated cell cultures will show which treatment curtails proliferation the most.

The present invention also relates to kits that are suitable for use in practicing the methods of the present invention. The kits can include a first ligand that recognizes a marker protein found at a specific cellular location and a second ligand that recognizes a marker protein found at the specific cellular location. Optionally, additional ligand that recognize additional marker proteins, whether at the same cellular location or at a different cellular location can also be included. The kit may also include first and second labeling reagents. The first labeling reagent binds specifically to the first ligand, and, when exposed to a first chromogen, forms a first pigment having a color. The second labeling reagent binds specifically to the second ligand, and, when exposed to a second chromogen, forms a second pigment having a color that is distinct of the color of the first pigment. Importantly, as noted above, upon co-localization the two pigments generate a distinct, intermediate color. The kits of the invention may also include additional components including, without limitation, instructions for carrying out the IHC analyses of the present invention; a compact disc or other computer readable media that includes computer code which, upon implementation by a suitable machine having a processor, will carry out the automated labeling and scoring of cells in accordance with the invention; and additional reagents such as rinsing agents, buffers, and the like.

EXAMPLES

The Examples set forth below are for illustrative purposes only and are not intended to limit, in any way, the scope of the present invention.

Example 1

Bone Marrow Specimen Procurement

Bone marrow specimens were obtained from volunteers without hematological disease at the Hospital for Special Surgery and from multiple myeloma patients at the New York-Presbyterian Hospital under informed consent as part of an Institutional Review Board approved study. The posterior and superior iliac spines were identified before beginning the procedure. The patient was placed in a ventral or lateral decubitus position. The field was cleaned with Betadine and the area of interest was anesthetized with 1% Lidocaine. A bone marrow aspirate and biopsy was performed unilaterally using a modified Jamshidi bone marrow aspiration/biopsy needle, 11 gauge×4 inch. Several 5-7 cc aspirates were obtained by relocating the needle in each aspirate to obtain a total of approximately 30 cc of marrow. The core biopsy was then obtained. The bone marrow core biopsies were fixed in 10% neutral-buffered formalin and paraffin-embedded.

Example 2

Immunohistochemistry Using Two Nuclear Biomarkers

Because cell cycle molecules are not unique to cancer cells and because some tumors are composed of cancer cells that coexist with large populations of non-cancer cells, in such tumors cell cycle analysis requires co-localization, detecting the cell cycle molecule in the cancer cells while excluding non-cancer cells from the analysis. For example, some tumors contain large numbers of actively proliferating immune cells; if they are not excluded from the analysis, assessment of proliferation may yield falsely high data.

In hematopoietic cancer biopsies, the non-cancer hematopoietic and immune cells must be excluded. In this example, multiple myeloma (MM) cells were identified in biopsy samples with an anti-MUM1 antibody and a detection system yielding a red signal. Specificity of MUM1 for myeloma cells in MM biopsies is estimated at ~99%, thus excluding non-MM cells from the analysis. Double IHC was performed to detect cell cycle molecules in situ in MM cells. Each slide was stained for MUM1 (above) using Bond™ Polymer AP Red Detection System (DS9305, Leica, Bannockburn, Ill.) to afford a red pigment, and for the cell cycle molecule with Blue Alkaline Phosphate Substrate Kit (Vector Laboratories, Burlingame, Calif.) to afford a blue pigment. The cell cycle molecules, including Ki67 and pSRb, are nuclear. With these particular chromogen systems, double staining yielded MM cells with either a red nuclear signal if the cell was not proliferating or a purple nuclear signal if the MM cells were proliferating (positive for the cell cycle molecule in question). Cells with a blue nuclear signal (negative for the cell cycle molecule in question) were non MM cells (FIG. 3A) that were proliferating.

To compute the percentage of MM cells expressing various cell cycle molecules, purple (MUM1+/cell cycle molecule+) cells were manually counted as a percentage of purple cells plus red (MUM1+/cell cycle molecule negative) cells. This manual method of analysis can be performed with any standard microscope.

To increase the accuracy, the same slides were first loaded in batches of 60 into an image analysis system, which performs photographic digital scans of each slide. Using an automatic image analyzer, the number of cells with a purple nucleus and those with a red nucleus in a given area was determined. The counts were performed in triplicate. The percentage of MM cells in the proliferative stage represented by the cell cycle molecule targeted is the number of purple cells divided by the number of purple and red cells. Expression of cell cycle molecules was uniform throughout the plasma cell population in most biopsies; in the rare biopsies that showed focal expression of a protein, the counts were performed in selected areas so as to best represent overall expression in the plasma cell population as a whole. The intensity of positive staining was scored in comparison to expression in B cells from serial sections of a single tonsil control slide, run in parallel with the marrow slides. The following cell types were used as positive controls for these respective proteins:

Germinal center B cells: Rb, phospho-Rb, p18, Ki-67
Naive B cells/mantle zone cells: p27
Basilar squamous epithelial cells: cyclin D3
Mantle cell lymphoma, primary sample with t(11; 14): cyclin D1

For each marker, expression was recorded as 0 (no staining), 1+(positive, but fainter than control), 2+ (equal to control), or 3+ (stronger than control).

IHC was performed on 4 micron sections of paraffin-embedded bone marrow tissues using a Leica Microsystems (Bannockburn, Ill.) Bond Max automated immunostainer. MUM1 MM cells were detected using an anti-MUM1 mouse monoclonal antibody (Mab) (Dako, Carpinteria, Calif.) and the Bond™ Polymer AP Red Detection System (Leica). Simultaneous expression of other proteins was detected with monoclonal antibodies to Ki-67, cyclin D1, cyclin D2, cyclin D3, MCM2, MCM7, skp2, p16, p18, p21, p27, Rb, c-myc, Cdk4 and Cdk6 and polyclonal rabbit antisera to either $pSer^{807/811}$, $pSer^{608}$ or $pSer^{780}$ of human Rb. When staining for phospho-proteins, tissue sections were pretreated with calyculin A (Cell Signaling Technology, Inc., Beverly, Mass.) to prevent de-phosphorylation during or after antigen retrieval; for negative controls, sections were treated with calf intestine phosphatase (Cell Signaling Technology, Inc., Beverly, Mass.) to verify phosphorylation. Rb null tumor sections (Rb-/Rb-) from ocular retinoblastoma cancers were used as negative controls for Rb staining. As a control for immunoglobulin synthesis, serial sections were stained with rabbit antibodies for IgM, IgD, IgG, IgA, Igκ and Igλ (Dako, Glostrup, Denmark). As positive controls, parallel analysis was performed on tissue sections containing, for example, centroblasts (Rb, phospho-Rb, p18, Ki-67); mantle zone B cells (p27); supra-basal squamous epithelial cells (cyclin D3) and mantle cell lymphoma with t(11; 14) (cyclin D1) (Ely et al., "Expression of CD56/Neural Cell Adhesion Molecule Correlates with the Presence of Lytic Bone Lesions in Multiple Myeloma and Distinguishes Myeloma from Monoclonal Gammopathy of Undetermined Significance and Lymphomas with Plasmacytoid Differentiation," *Am J Pathol* 160:1293-9 (2002); Ely et al., "Telomerase Activity in B-Cell Non-Hodgkin Lymphoma," *Cancer* 89(2):445-52 (2000); Ely et al., "Mutually Exclusive Cyclin-Dependent Kinase 4/Cyclin D1 and Cyclin-Dependent Kinase 6/Cyclin D2 Pairing Inactivates Retinoblastoma Protein and Promotes Cell Cycle Dysregulation in Multiple Myeloma," *Cancer Res* 65(24): 11345-53 (2005), which are hereby incorporated by reference in their entirety).

Example 3

Automated Image Analysis

The double stained IHC slides were accessioned into the image analysis system and then loaded onto the machine in batches of 60. A robotic arm picked up each slide, one at a time, and loaded it onto the microscope. Via a motorized stage, the microscope moves and scans the slide, looking for tissue, the location of which varies slightly from slide to slide. Once it has found the tissue, the device scans the tissue and the camera records low resolution images. Using the scanned low resolution images, the inventor selected ten good areas for subsequent high resolution scanning and analysis. Numerous data points were then calculated for each of the ten areas per slide, and those data were averaged.

Since no counterstain was used in these slides, all identifiable cells are positive for at least one marker (e.g., in FIG. 3A, cells that express neither MUM1 nor pSRb are not visible). The characteristics used for the analysis ("classifiers") were determined by a process whereby the inventor trained the software what was considered to be cells of each color. The software analyzed the high resolution images by first applying color parameters to decide if a nucleus was blue, red, or purple. It finds pixels within the appropriate range of color parameters as defined by hue, saturation, and intensity; objects too light or too dark, as determined by the classifiers, were not included in the analysis. It then analyzed adjacent pixels to determine which appropriately stained objects were nuclei by applying the size and shape parameters (spot width, width, compactness, roundness and axis ratio) set by the inventor. Red nuclei were labeled with an asterisk, and purple nuclei were labeled with a circle. An example of the outcome of this analysis is shown in FIG. 3B.

Figure 9:
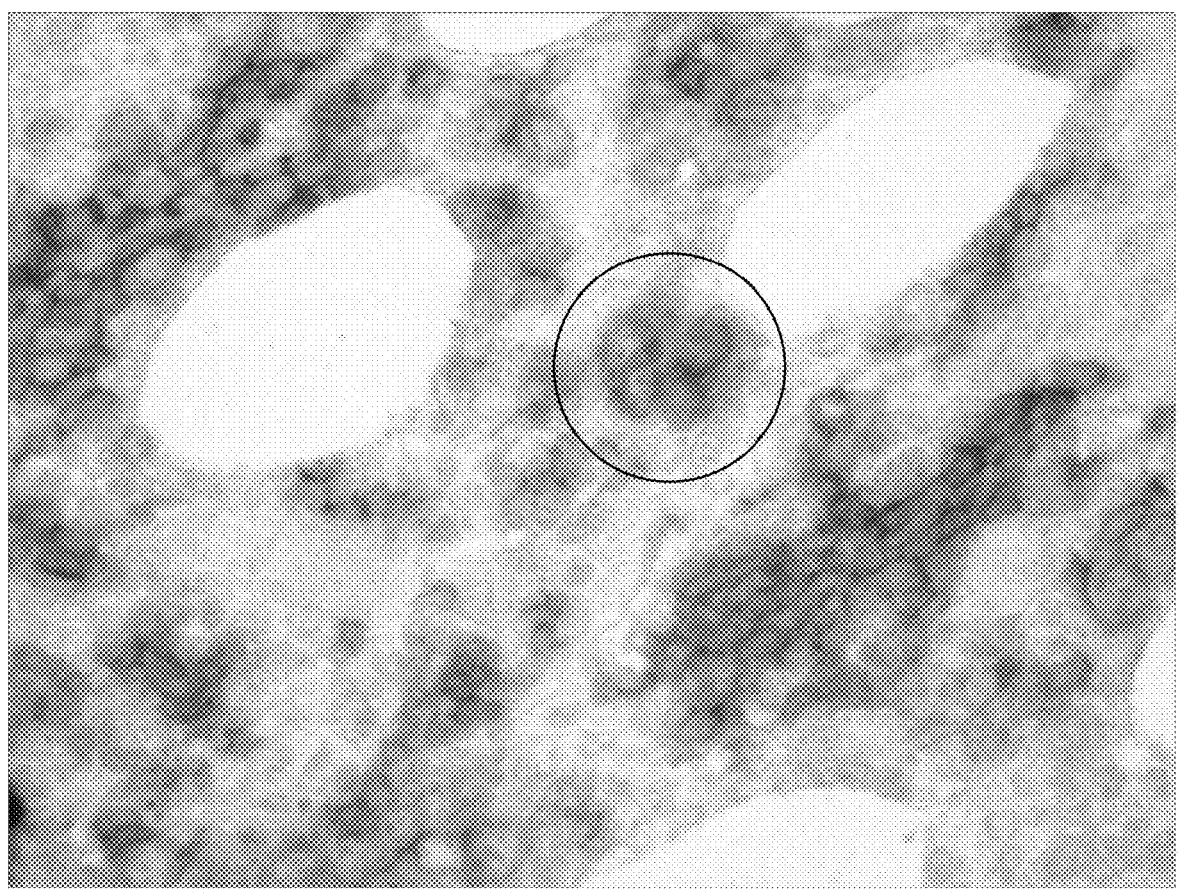
FIGS. 9 and 10 are images of histological biopsy samples from two patients to assess minimal residual disease after therapy for acute myeloid leukemia (AML) as observed under light microscope. In these samples, the proteins detected are membranous (localized to the cytoplasmic membrane). Leukemic cancer cells express the cytoplasmic membrane antigen, CD117 (c-kit), which is stained with a chromogen affording a blue pigment (Blue Alkaline Phosphate Substrate Kit produced by Vector Laboratories, Burlingame, Calif.). However, the usefulness of conventional, single-color immunostaining for CD117 is limited by the fact that non-leukemic erythroid precursor cells in a recovering bone marrow also express CD117. The non-leukemic erythroid cells express glycophorin C, which is not expressed by the leukemic cells. Staining for glycophorin C was carried out using a chromogen affording a red pigment (Bond™ Polymer AP Red Detection System, DS9305, Leica, Bannockburn, Ill.). Utilizing dual staining for these two membrane-bound proteins allows for distinguishing between leukemic blasts, with blue membranes (CD117$^+$/glycophorin C(neg.)) and benign erythroid progenitors, with purple membranes (CD117$^+$/glycophorin C$^+$). In the first patient (FIG. 9), residual disease is detected as a cluster of four large cells with blue cytoplasmic membranes (encircled). In the second patient (FIG. 10), the presence of residual disease is excluded; there are cells with purple (CD117$^+$/glycophorin C$^+$) membranes, but none with blue membranes.
Figure 10:
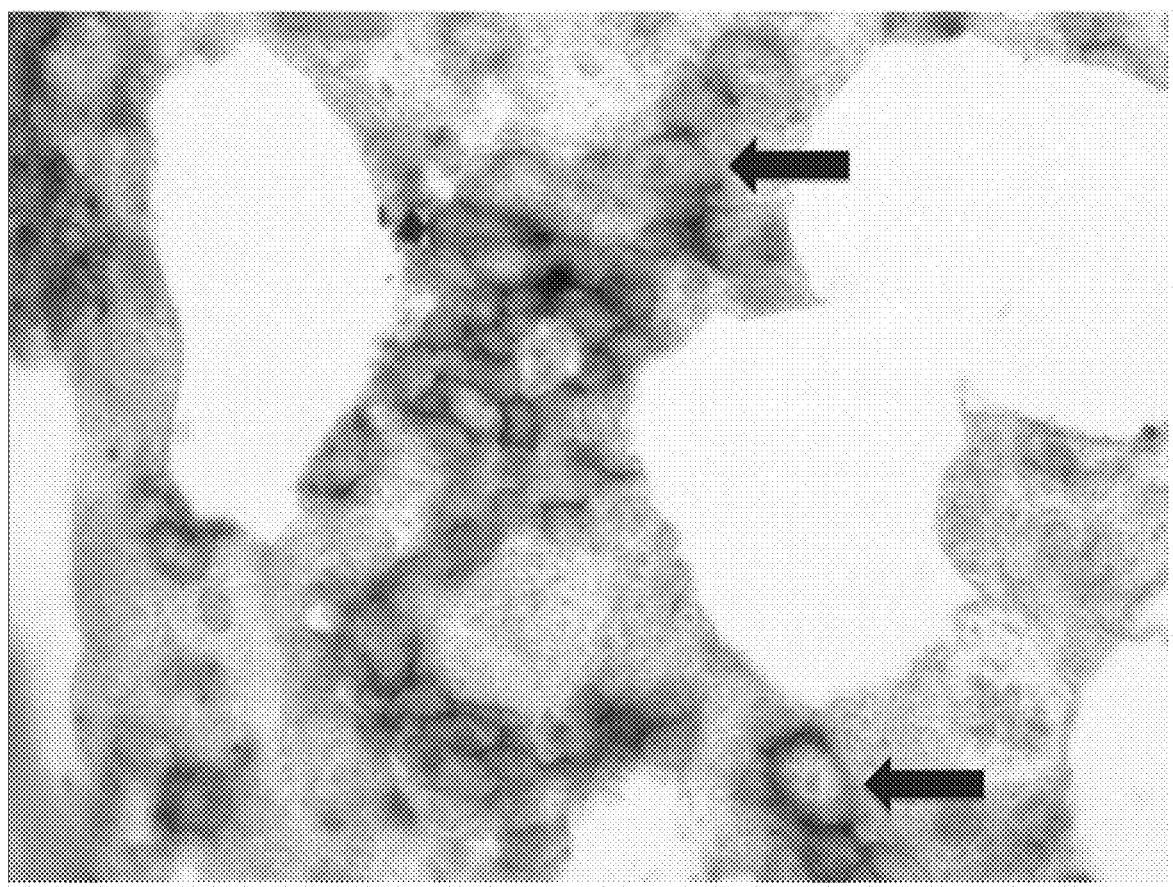

The process detailed in this example was later modified to assess co-localization to cell membranes, as shown in FIGS. 9 and 10.

Example 4

Exploring the Efficacy of a Drug Treatment

Figure 4:
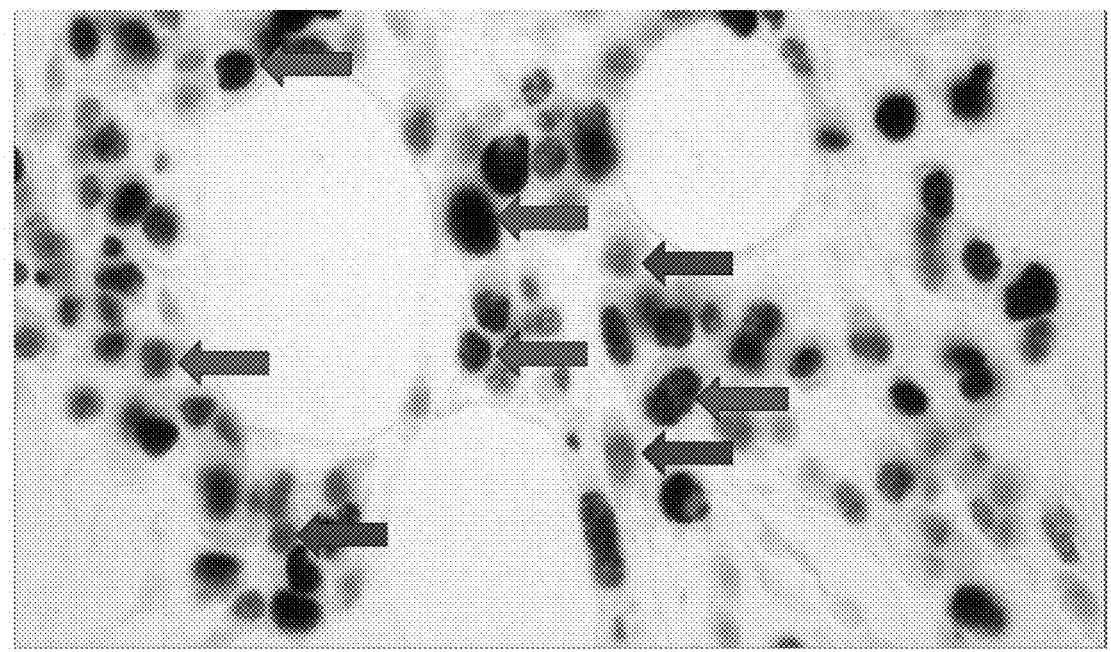
FIG. 4 is an image of a histological bone marrow biopsy sample taken from a multiple myeloma (MM) patient prior to single drug therapy with a specific inhibitor of Cdk4/6. Because Cdk4/6 specifically phosphorylates Rb at serine 807/811 (resulting in $pS^{807/811}Rb$), the invention is used to measure $pS^{807/811}Rb$ and its downstream protein, Ki67, in MM cells before and during therapy. In this sample, the nuclear protein, MUM1, a biomarker for MM cells, has been stained with a chromogen affording a red pigment. In addition, the nuclear Ki67 protein, a biomarker of progression into the S, G2, or M phase, has been stained with a chromogen affording a blue pigment. Cells exhibiting red nuclei are non-cycling MM cells (red arrows). Cells with blue nuclei are non-MM hematopoietic marrow cells that are cycling, i.e., have started to proliferate. Cells with purple nuclei show co-localization of the two markers and represent MM cells cycling in the S, G2, or M phase (purple arrows).
Figure 5:
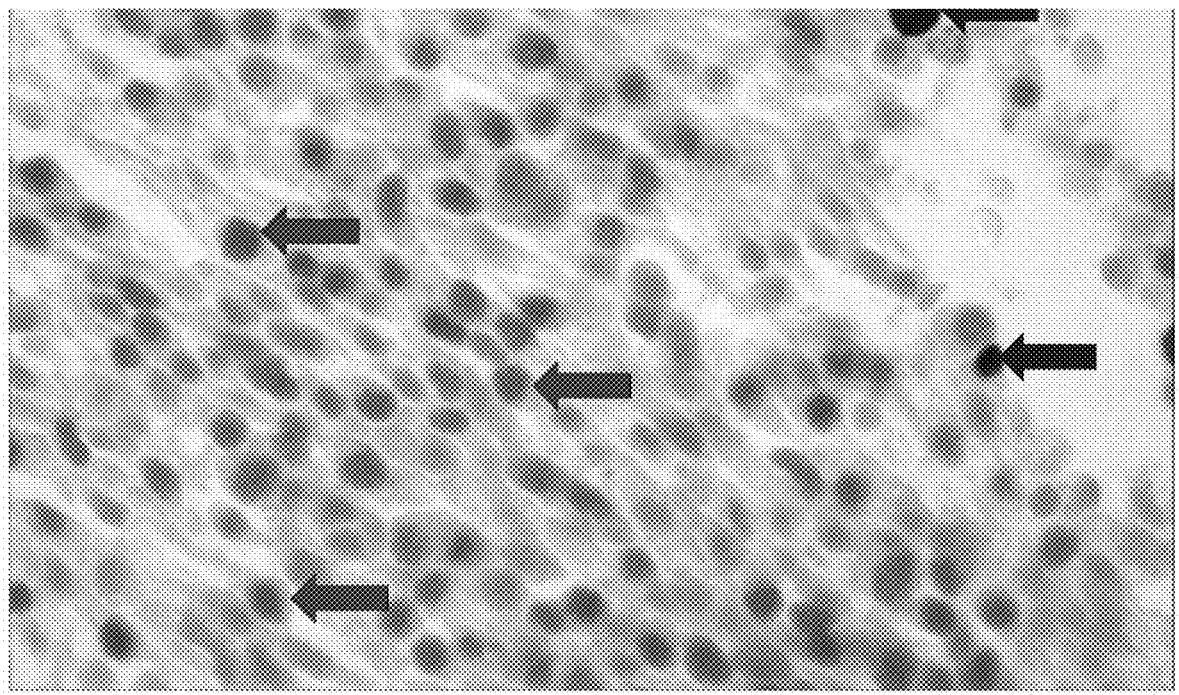
FIG. 5 is an image of a histological bone marrow section from a biopsy sample taken from the same patient with the same staining conditions as FIG. 4. This sample was obtained after the patient was treated for 8 days with a CDk4/6 inhibitor. The sample shows that the MM cells are no longer cycling (i.e., have become Ki67 negative), and this patient is responding to the drug therapy.
Figure 6:
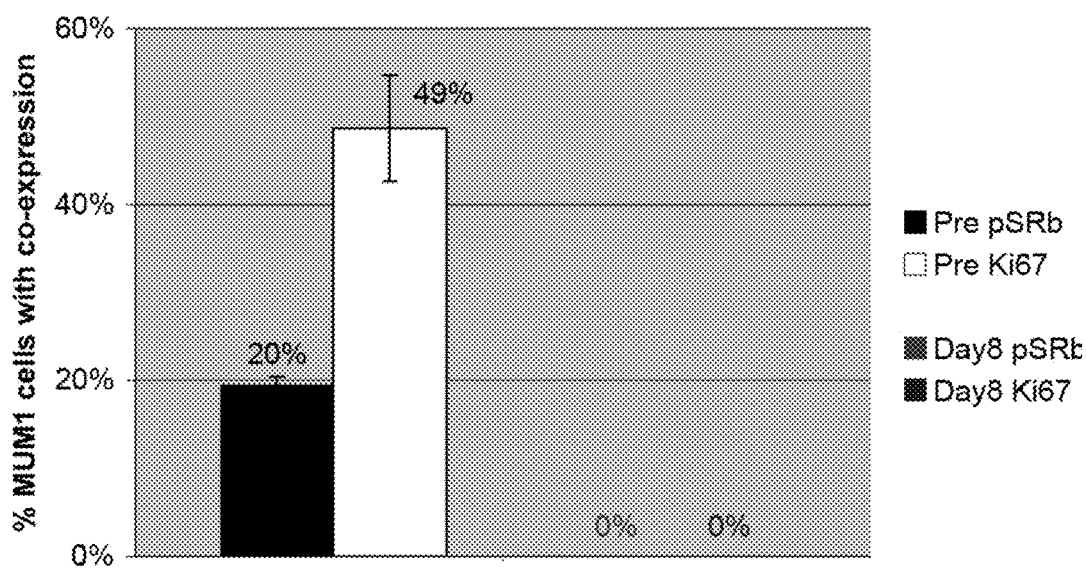
FIG. 6 is a graph comparing IHC results of bone marrow from the patient of FIGS. 4 and 5 using two different cell cycle protein markers, phospho-Rb and Ki67. Because pS-Rb is only present in late G1 and S phase, it is typically found in fewer cells than Ki67, which is present in S, G2, and M phases because it has a long half-life. Ki67 can even be identified in G0 cells that have recently exited the cycle. However, both markers indicate there are no cycling MM cells after this treatment.

As part of an IRB-approved phase I/II clinical trial, patient bone marrow biopsies were performed before and after treatment with the selective early G1 cell cycle inhibitor PD-332991 for 8 days and analyzed by the method of this invention using anti-MUM1 monoclonal antibodies and anti-Ki67 or anti-pSRb, as described in Examples 1-3. The MM cells were localized by anti-MUM1 antibodies, detected with the Bond™ Polymer AP Red Detection System (affording red pigment) and the cell cycle proteins were detected with the Vector® Blue Alkaline Phosphate Substrate Kit III, SK-5300 (affording blue pigment). Non-MM cells were excluded from the analysis by lack of MUM1 expression. The analyses for MM cells (MUM1 positive) expressing Ki67 before and after treatment are displayed in FIGS. 4 and 5, respectively. FIG. 6 is a graph comparing the results of this drug treatment obtained with anti-pSRb and anti-Ki67. Both markers indicate great efficacy for PD-332991 in stopping the cell cycle at the given dosage.

Also, biopsies were performed 6 days after cessation of drug administration and showed that the MM cells returned to cycling in percentages comparable to what was observed prior to treatment. The invention has so far shown similar efficacy in 11/11 (100%) of MM patients. Because the method of the invention is the only way to accurately assess the efficacy of this drug, in situ, it will be employed throughout the remainder of phase I, into phase II and, permission granted, in phase III.

Example 5

Monitoring the Drug Response of a Lymphoma Patient

In this example, the drug response of a patient with B cell lymphoma to a therapy was monitored as part of an IRB approved phase I trial. The therapy being tested was the Cdk4/6 inhibitor, PD-332991, described in Example 4. If the drug is working in a patient, it will cause a reduction of phosphorylation of a serine in the retinoblastoma (Rb) protein. One such Rb phosphorylation site is at the 807/811 serine. There also should be a reduction (though less) in the downstream proliferation protein, Ki67. As a broader assessment of drug effect, it is helpful to look at both the direct target and a downstream target. PAX5 (red pigment in all images) is a nuclear antigen present in B cell lymphomas. In this assay, all lymphoma nuclei appear red. The cell cycle proteins ($pS^{807/811}Rb$ and Ki67) were detected by a blue pigment. In the resultant slides, a lymphoma cell (red) that is cycling (blue) attains a double stained nucleus (purple); because there is no nuclear counter stain, non-lymphoma/non-cycling cells (e.g., immunologic cells such as T cells) are not visible. The output is the percentage of cycling lymphoma cells (purple) as a percentage of all lymphoma cells (purple+red). This output can be assessed by manual cell counting as performed in any standard microscope. For greater accuracy, a far larger number of cells can be assessed by image analysis (similar to that described in Example 3).

As shown in FIGS. 7A-B and measuring by image analysis, Rb phosphorylation by Cdk4/6 at serine 807/811 ($pS^{807/811}Rb$) was found in 84.08% of lymphoma cells before treatment but was reduced successfully to only 2.14% by day 21 of therapy (arrow at right indicates $pS^{807/811}Rb^+$ lymphoma cell (purple nucleus) in a group of negative lymphoma cells (red nuclei)). As shown in FIGS. 7C-D, there was also a drop in Ki67 expression, from 97.52% of lymphoma cells prior to treatment, to 23.13% on day 21. A response of this magnitude signals that this specific patient responded to the treatment, as assessed in vivo at the single cell level. A clinician can use this data to decide whether or not to keep a patient on the trial. These results correlate well with patient FLT-PET scanning, which assesses uptake of thymidine by tissues. However, the method of the invention was found to be more reliable and far less costly than PET.

Example 6

Diagnosis of Plasma Cell Neoplasm

Figure 2:
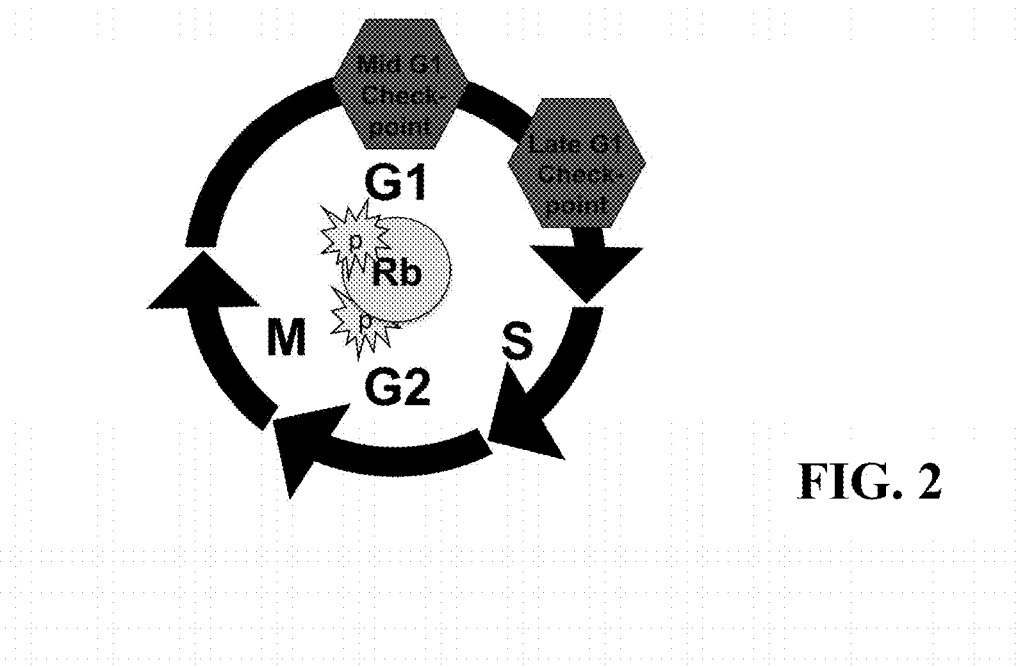
FIG. 2 is a schematic that illustrates stages of the cell cycle. G1 and G2 stand for 'gaps'. This refers to the fact that nothing obvious is occurring in the nucleus during these stages. The cells are actually very active. They are growing and preparing to divide. S stands for synthesis. This is the phase of the cell cycle in which the DNA is copied, in anticipation of each subsequent daughter cell needing a copy after division. M stands for mitosis. This is the stage of the cell cycle in which the cell divides into two daughter cells. Cell cycle progression is controlled primarily at two checkpoints in mid-G1 and late-G1. Passing each checkpoint requires phosphorylation of the retinoblastoma protein (Rb). When Rb is completely phosphorylated, the cell will enter S phase.

Cell proliferation requires entering the cell cycle, which is controlled mainly in G1 (FIG. 2). Although progression past the mid-G1 checkpoint occurs due to phosphorylation of the Rb protein by Cdk4 or CDk6, for these kinases to function they must be bound to a D cyclin (cyclin D1, cyclin D2 or cyclin D3). Which D cyclin is expressed depends on cell lineage. Normal plasma cells rarely proliferate, but when they do, they utilize cyclin D2. Expression of D1 or D3 in plasma cells is diagnostic of neoplasia (Ely et al., "Mutually Exclusive Cyclin-Dependent Kinase 4/Cyclin D1 and Cyclin-Dependent Kinase 6/Cyclin D2 Pairing Inactivates Retinoblastoma Protein and Promotes Cell Cycle Dysregulation in Multiple Myeloma," *Cancer Res.* 65:11345-11353 (2005), which is hereby incorporated by reference in its entirety). Because the invention allows detection of co-expression of cyclin D1 with MUM1, it can be used to diagnose plasma cell neoplasms, if they overexpress D1 or D3 (total of ~70% of cases).

Figure 8:
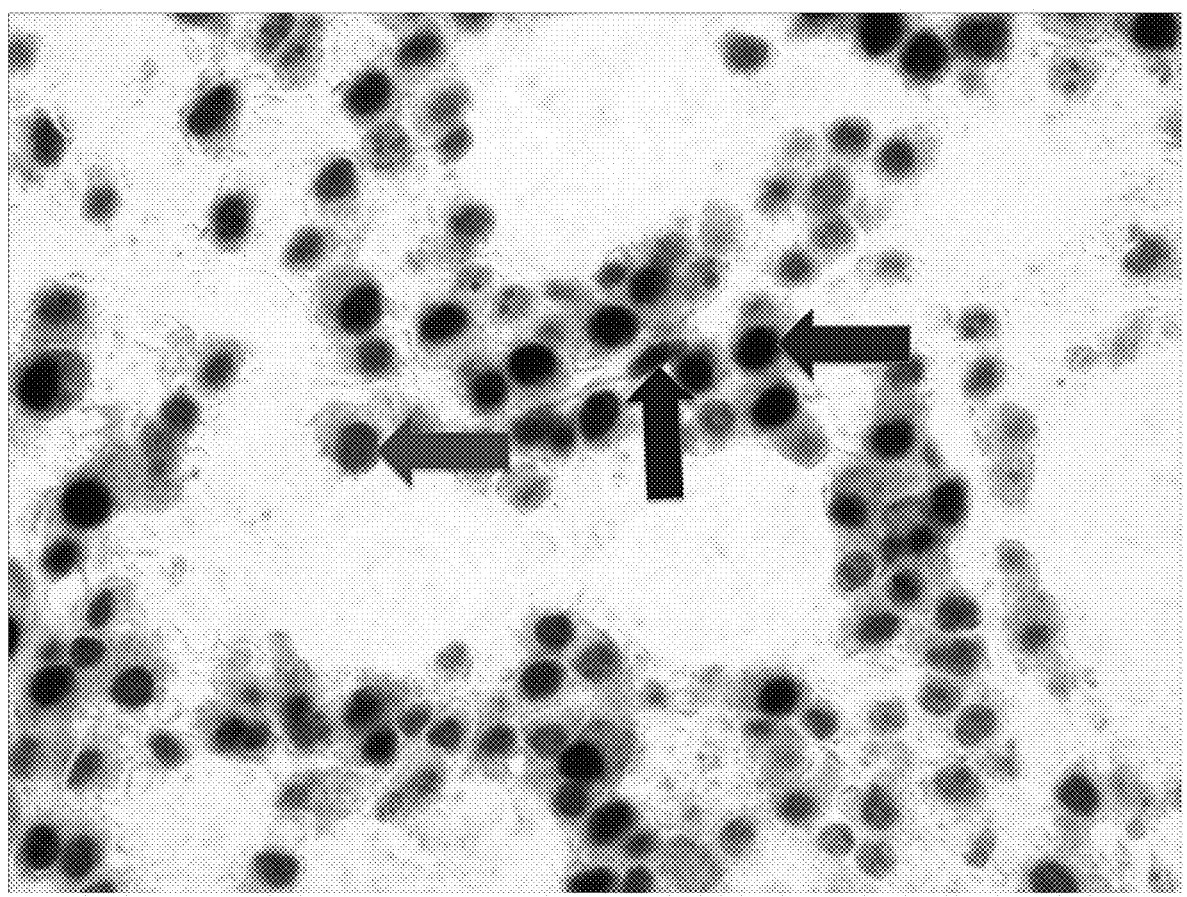
FIG. 8 is an image of a histological bone marrow section from a biopsy sample, which was used for diagnosing a plasma cell neoplasm. Cyclin D1 is not expressed in any non-neoplastic plasma cells, but is aberrantly expressed in some PC neoplasms, such as due to increased copy numbers of chromosome 11, where the cyclin D1 gene resides. Finding any plasma cells that express cyclin D1 is diagnostic of a plasma cell neoplasm. In this image, cyclin D1 is stained with a chromogen affording a blue pigment (Blue Alkaline Phosphate Substrate Kit produced by Vector Laboratories, Burlingame, Calif.) and MUM1 with a chromogen affording a red pigment (Bond™ Polymer AP Red Detection System, DS9305, Leica, Bannockburn, Ill.), resulting in MUM1$^+$/D1 (neg.) normal plasma cells being red (red arrow), MUM1$^+$/D1$^+$ co-expression being purple (purple arrow), and MUM1 (neg.)/D1$^+$ spindle shaped stromal cells being blue (blue arrow). Cells expressing neither D1 nor MUM1 do not show up, because there is no counterstain. In this patient, clinically suspected of having a plasma cell neoplasm, finding cyclin D1 co-expression in a population of plasma cells is diagnostic of neoplasia.

D cyclin expression analysis is less reliable and less sensitive by conventional, single color IHC; for example, cyclin D1 is normally expressed by some cells other than PCs in BM and distinction of which cell type is expressing D1 is not reliable by conventional IHC. Like other cancers, chromosomal abnormalities are common in MM and in the pre-cancerous neoplasm MGUS (monoclonal gammopathy of undetermined significance). The most common recurrent chromosomal translocation in plasma cell neoplasms (occurring in ~25% of both MGUS and MM) is t(11; 14), in which the cyclin D1 gene (on chromosome 11) becomes constitutively overexpressed. Similarly, cyclin D3 (on chromosome 6) becomes constitutively overexpressed in ~5% of MM via the t(6; 14). These data were derived by gene chip microarray (Bergsagel et al., "Molecular Pathogenesis and a Consequent Classification of Multiple Myeloma," *J Clin Oncol.* 23(26):6333-6338 (2005), which is hereby incorporated by reference in its entirety). However, because gene array is so costly and labor intensive, even though it has been commercially available for >10 years, its use is strictly limited to the research setting. Although gene array is not suitable for routine diagnosis, the invention allows the detection and quantification of D cyclin expression, in situ, at the single cell level. Moreover, because the method of the invention can be performed in any immunohistochemistry lab, it has the real potential of widespread use. In t(11; 14), there is strong uniform expression of cyclin D1 in nearly all the cells. In another scenario, hyperdiploidy with increased copies of chromosome 11 (~40% of plasma cell neoplasms), there also is overexpression of cyclin D1, but of variable intensity, and only in a subpopulation of the neoplastic cells (FIG. 8).

Example 7

Assessment of Residual Disease Following Cancer Treatment

Biopsy samples were obtained from ten acute myeloid leukemia (AML) patients following treatment, and histological samples were prepared using standard techniques.

The dual-staining procedure of the invention was used to detect residual AML using light microscopy with staining of CD117 using a chromogen forming a blue pigment (Blue Alkaline Phosphate Substrate Kit produced by Vector Laboratories, Burlingame, Calif.) and glycophorin C using a chromogen forming a red pigment (Bond™ Polymer AP Red Detection System, DS9305, Leica, Bannockburn, Ill.). Leukemic blasts were detectable by the presence of blue membranes (CD117$^+$/glycophorin C(neg.)) and were distinguishable from benign erythroid progenitors having purple membranes (CD117$^+$/glycophorin C$^+$). In the first patient (FIG. 10), residual disease was detected as a cluster of four large cells with blue cytoplasmic membranes (FIG. 9, encircled). In the second patient, the presence of residual disease was excluded by the absence of cells with blue membranes—only normal cells having purple (CD117$^+$/glycophorin C$^+$) membranes were observed.

Example 8

Assessment of Immune Response in Antigen-Exposed Tissue

A histological sample was taken from a human tonsil (IRB-approved patient consent was obtained).

Figure 11:
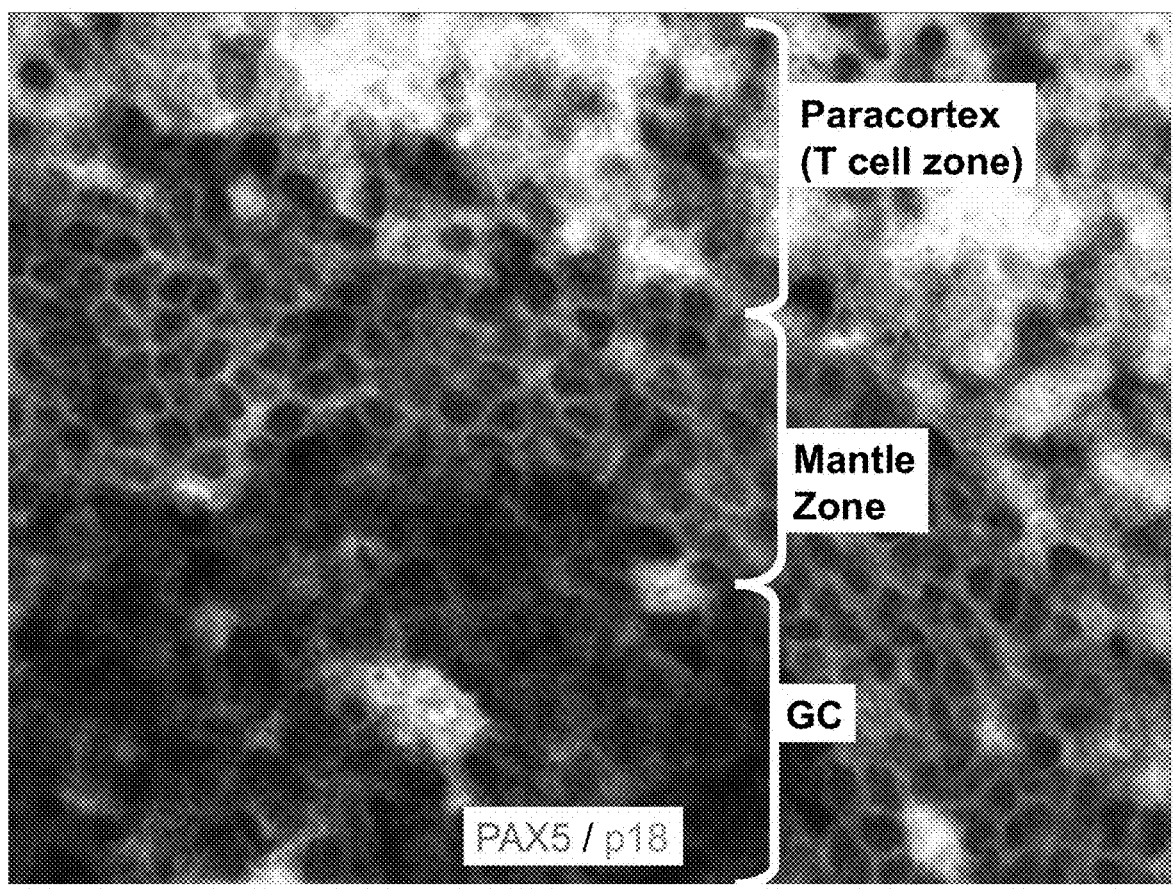
FIG. 11 is an image of a histological sample taken from a human tonsil (IRB-approved patient consent was obtained). The sample was used to assess the roll of cell cycle regulation in the human immune response, as detected using light microscopy. After exposure to common oral antigens (e.g., food and bacteria), a human tonsil sample was stained for PAX5, a B cell antigen, using a chromogen affording a red pigment (Bond™ Polymer AP Red Detection System, DS9305, Leica, Bannockburn, Ill.) and p18, a cell cycle inhibitor, using a chromogen affording a blue pigment (Blue Alkaline Phosphate Substrate Kit produced by Vector Laboratories, Burlingame, Calif.). Shown are three zones of tonsil cells, the paracortex (primarily T lymphocytes), the mantle zone (naïve B cells, not yet exposed to antigens), and the germinal center (B cells actively undergoing the process of reacting to antigen stimulation). The staining procedure shows that the paracortex contains mainly PAX5(neg)/p18$^+$ T cells (blue) or cells expressing neither PAX5 nor p18

The dual-staining procedure of the invention was used to assess the roll of cell cycle regulation in the human immune response, as detected using light microscopy. After exposure to common oral antigens (e.g., food and bacteria), the human tonsil sample was stained for the B cell antigen PAX5 using a chromogen forming a red pigment (Bond™ Polymer AP Red Detection System, DS9305, Leica, Bannockburn, Ill.) and the cell cycle inhibitor p18 using a chromogen forming a blue pigment (Blue Alkaline Phosphate Substrate Kit produced by Vector Laboratories, Burlingame, Calif.). Shown in FIG. 11 are three zones of tonsil cells: the paracortex, the mantle zone, and the germinal center. The staining procedure shows that the paracortex contains mainly PAX5(neg)/p18$^+$ T cells (blue) or cells expressing neither PAX5 nor p18 (PAX5(neg)/p18(neg), colorless areas). By contrast, the mantle zone contains mainly PAX5$^+$/p18(neg) naïve B cells (red) that have not yet been exposed to antigens. The germinal center, however, contains mainly PAX5$^+$/p18$^+$ B cells (purple) that are actively undergoing maturation in response to antigen stimulation. This confirms published data, showing the role of p18 in B cell maturation to the fully mature plasma cell stage (Tourigny et al., "CDK Inhibitor p18 (INK4c) Is Required for the Generation of Functional Plasma Cells," *Immunity* 17:179-189 (2002), which is hereby incorporated by reference in its entirety).

Example 9

Predicting Transformation for Pre-Malignant to Malignant Plasma Cell Neoplasms

Normal PCs and MGUS cells do not express the cell membrane protein CD56. However, CD56 overexpression occurs with transformation to MM (Ely et al., "Expression of CD56/Neural Cell Adhesion Molecule Correlates with the Presence of Lytic Bone Lesions in Multiple Myeloma and Distinguishes Myeloma from Monoclonal Gammopathy of Undetermined Significance and Lymphomas with Plasmacytoid Differentiation," *Am J Pathol.* 160:1293-1299 (2002), which is hereby incorporated by reference in its entirety). Because the double-staining process of the invention allows co-localization of CD56 with a membranous protein that is expressed exclusively by PCs in adult marrow, CD138 (Syndecan 1), a patient with MGUS (CD138$^+$/CD56 neg.) can be monitored for the advent of CD56 co-expression, which occurs upon transformation to MM. Because CD56 expression portends the formation of lytic bone lesions, this finding can be used as a trigger to consider treating a patient.

Example 10

Discover Predictors of Response to Proteosome Inhibitor Regimen

Expression of the cyclin dependent kinase inhibitor, p18, has been shown to be necessary for cessation of the cell cycle in plasma cells (Tourigny et al., "CDK Inhibitor p18(INK4c) Is Required for the Generation of Functional Plasma Cells," *Immunity* 17:179-189 (2002), which is hereby incorporated by reference in its entirety). The invention was used to analyze specimens in a clinical trial of a proteosome inhibitor regimen for treatment of MM (Niesvizky et al., "BIRD (Biaxin [clarithromycin]/Revlimid [lenalidomide]/dexamethasone) Combination Therapy Results in High Complete- and Overall-Response Rates in Treatment-naive Symptomatic Multiple Myeloma," *Blood* 111:1101-1109 (2008), which is hereby incorporated by reference in its entirety). Using the double-staining IHC process of the invention, it was discovered that expression of p18 correlates with clinical response. Co-expression of p18 with MUM1 was found in an average of 18% of MM cells in patients with a good response vs. only 4% in patients with a poor response. An ex vivo analysis of patient cells confirmed this finding. Biochemical experiments showed that p18 expression enhances response by slowing the cell cycle, by which mechanism it is synergistic with proteosome inhibitors.

Example 11

Predict Time to Progression in Multiple Myeloma

The plasma cell labeling index (PCLI) uses BrdU labeling as a measure of plasma cell proliferative activity and has been shown to predict poor prognosis in newly diagnosed multiple myeloma (MM) patients. Major drawbacks of this technique include the following: it is time-consuming and labor intensive, it requires a degree of subjectivity in its interpretation, it requires a dark room fluorescence facility, and it can only be performed on viable cells in liquid suspension. Because of these limitations, PCLI was described more than 20 years ago but is only used routinely in a single hospital today. Side by side comparison has shown that using double-staining IHC process of the present invention to assess MM cell proliferation (in core biopsies using Ki-67/MUM1 staining as described in Examples 2 and 4) is more accurate and reproducible. Moreover, because it is used on fixed biopsies and can be performed in any lab that does IHC, it is feasible for widespread use.

High-dose pulsed dexamethasone (Dex) is one of the preferred treatments for relapsed MM patients and is currently the accepted gold standard against which investigational drugs are being tested. The predictors of outcome for relapsed patients while on Dexamthasone (Dex) treatment have not been well established. These predictors were prospectively evaluated using the Ki-67/MUM1 markers in patients with relapsed MM receiving Dex in consecutive, prospective clinical trials. Time to progression is defined as date of Dex initiation to date of progressive disease (PD). Sixteen patients with relapsed MM were evaluated. Of the 16 patients, 56% (n=9) showed progressive disease at a median time of 87 days. The median Ki67 for those patients with PD was 2.8, while Ki67 for those that did not show PD was 0.80. Cox-regression analysis revealed a 1.5 times greater likelihood of progression per unit increase in PCLI (p=0.07). These results support the clinical utility of the invention in predicting which patients will progress after high-dose Dex treatment.

Example 12

Predicting Survival after Bone Marrow Transplantation

Bone marrow specimens were collected prior to therapy as part of an IRB-approved clinical trial of tandem bone marrow transplantation (BMT) for MM patients. The biopsies were formalin fixed, paraffin embedded and archived at room temperature in a standard facility used to house routine pathologic specimens. Patients were treated in 1994-1995 and followed since.

In a retrospective analysis, the dual-staining process of the present invention was used to assess proliferation in MM cells prior to therapy by co-localization of MM/Ki67. The method of the invention showed a correlation between Ki67 and actual survival. Patients alive today had a median Ki67 of 0.00% prior to therapy as compared to 6.30% in deceased patients (p=0.0006 by t-test). Unlike other methods, these data show that the invention can be used retrospectively to analyze routinely preserved and archived specimens 15 years old and perhaps older.

Example 13

Tumor Cell Specific Proliferation in Glioblastoma Multiforme, Lung, Thyroid and Breast Carcinomas Glioblastoma multiforme ("GBM") is a brain cancer. Therapy with drugs, radiation, surgery or palliation is instituted on the basis of clinical judgment. Although the cancer cell of origin is glial, histologic examination of the tumors shows an admixture of glia with inflammatory cells and neurons. Although assessment of proliferation has not shown great results in terms of prognosis or predicting treatment response, the methods employed have not allowed exclusion of non-glial/non-cancer cells from analysis.

The dual-staining process of the present invention was used to assess tumor-cell specific proliferation in 5 GBM patients. Triple staining was performed with NeuN, a neuronal nuclear antigen, using a chromogen forming a red pigment (Bond™ Polymer AP Red Detection System, DS9305, Leica); PU.1, a myeloid/inflammatory cell antigen, using a chromogen forming a red pigment (Bond™ Polymer AP Red Detection System, DS9305, Leica); and Ki67 using a chromogen forming a blue pigment (Blue Alkaline Phosphate Substrate Kit produced by Vector Laboratories). Tumor cell proliferation was assessed as all cells with blue nuclei; non-tumor proliferating cells were excluded by their purple color (NeuN$^+$/Ki67$^+$ neurons or PU.1$^+$/Ki67$^+$ inflammatory cells). This demonstrates the feasibility of using the invention in GBM.

The dual-staining process of the present invention is currently being used to assess tumor-cell specific proliferation in 5 lung cancers and 5 thyroid cancers. Both of these types of cancer show tumor cell specific expression of the same protein, thyroid transcription factor 1 (TTF1). TTF1 is being stained using a chromogen forming a red pigment (Bond™ Polymer AP Red Detection System, DS9305, Leica); and Ki-67 is being stained using a chromogen forming a blue pigment (Blue Alkaline Phosphate Substrate Kit produced by Vector Laboratories). Tumor cell specific proliferation is being assessed as the percentage of purple cells (TTF1$^+$/Ki67$^+$) divided by all tumor cells (red TTF1$^+$/Ki67 neg. cells plus purple cells). Preliminary results demonstrate the feasibility of using the invention in non-hematopoietic cancers.

Finally, dual-staining process of the present invention has been used to assess proliferation in estrogen-receptor-positive (ER$^+$) breast cancer cells. Although anti-estrogen therapy is efficacious in some ER$^+$ breast cancer patients, others do not respond as well. Currently, anti-estrogen therapy is instituted routinely in most ER⁺ patients; ER expression is typically assessed by single color standard IHC.

To assess whether the present invention can better predict the efficacy of anti-estrogen therapy, biopsy samples were obtained from five patients and analyzed for ER using a chromogen forming a red pigment (Bond™ Polymer AP Red Detection System, DS9305, Leica) and Ki-67 using a chromogen forming a blue pigment (Blue Alkaline Phosphate Substrate Kit produced by Vector Laboratories). Based on the staining of these markers, it is possible to compute the ER⁺/Ki67⁺ breast cancer cell-specific proliferation index as a percentage of all ER⁺ cells (purple ER⁺/Ki67⁺ cells divided by purple cells plus red cells (which are ER⁺/Ki67 neg.). It was determined that the percentage of ER⁺/Ki67⁺ cells differed from the percentage of all Ki67⁺ cells in most cases, which indicates that the method should be a better predictor of response to anti-estrogen therapy than the current, standard single color IHC.

All of the features described herein (including any accompanying claims, abstract and drawings), and/or all of the steps of any method or process so disclosed, may be combined with any of the above aspects in any combination, except combinations where at least some of such features and/or steps are mutually exclusive.

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. Additionally, the recited order of processing elements or sequences, or the use of numbers, letters, or other designations therefore, is not intended to limit the claimed processes to any order except as may be specified in the claims. These alterations, improvements, and modifications are intended to be suggested hereby, and are within the spirit and scope of the invention. Accordingly, the invention is limited only by the following claims and equivalents thereto.

What is claimed:

1. A method for immunohistochemistry analysis of specific cell populations in tissue samples containing heterogeneous populations of cells, said method comprising:
   providing a fixed, histological lymphoid or bone marrow tissue sample;
   exposing the provided lymphoid or bone marrow tissue sample to first and second primary antibodies, or antigen-binding fragments thereof comprising all complementarity determining regions of the respective primary antibody, that recognize, respectively, (i) a cancer cell marker protein found within a nucleus that is selected from the group consisting of MUM1 (IRF4), PAX5, bcl-6, TdT, and thyroid transcription factor, and (ii) a cell cycle marker selected from the group consisting of pS-Rb, Ki67, MCM2, MCM7 and skp2, thereby forming an antibody-labeled sample;
   exposing the antibody-labeled sample to first and second secondary antibodies, or antigen-binding fragments thereof comprising all complementarity determining regions of the respective secondary antibody, the first secondary antibody, or antigen-binding fragment thereof, binding to the first primary antibody, or antigen-binding fragment thereof, and the second secondary antibody, or antigen-binding fragment thereof, binding to the second primary antibody, or antigen-binding fragment thereof, the first and second secondary antibodies, or antigen-binding fragments thereof, each comprising a reagent for forming distinct pigments;
   exposing the resulting sample to one or more chromogenic substrates for the reagents of the first and second secondary antibodies, or antigen-binding fragments thereof, thereby forming one pigment in nuclei containing the cancer cell marker protein and another pigment in nuclei containing the cell cycle marker or regulator protein, or both pigments in nuclei containing both the cancer cell marker protein and the cell cycle marker or regulator protein; and
   using light microscopy, identifying the number of cells that display only one particular pigment, or more than one pigment, by the different coloration of nuclei labeled by the distinct pigments, wherein the nuclei are further identified by one or more of size, shape, and aspect ratio.

2. The method according to claim 1, wherein the cancer cell marker protein is MUM1, and the cell cycle marker or regulator protein is Ki-67 or pS-Rb.

3. The method according to claim 1, wherein the reagent of the first and second secondary antibodies or antigen-binding fragments thereof comprises an enzyme that acts on a chromogenic substrate to form the first and second pigments, respectively.

4. The method according to claim 1, wherein the pigments are of distinct but inherently mergeable colors, and when co-localized the pigments give a distinctive intermediate color.

5. The method according to claim 3, wherein one pigment is red, the other pigment is blue, and the intermediate color is purple.

6. The method according to claim 1 wherein the lymphoid or bone marrow tissue sample contains a heterogeneous population of non-neoplastic and neoplastic cells.

7. The method according to claim 1 further comprising:
   determining the percentage of cells that exhibit both pigments in the cell population that is the sum of cells that exhibit one or both pigments.

8. The method according to claim 1, wherein the specific cell populations in the sample for analysis are cancer cells.

9. The method according to claim 8, wherein the cancer cells are selected from the group of acute myelogenous leukemias (AML); acute promyelocytic leukemia (APL); myeloproliferative disorders (MPD), including chronic myelogenous leukemia (CML) and polycythemia vera; all myelodysplastic syndromes (MDS) and myelodysplastic/myelo-proliferative diseases; all acute lymphoblastic leukemias (ALL), including precursor B-lymphoblastic leukemia/lymphoma and precursor T lymphoblastic leukemia/lymphoma; chronic lymphocytic leukemia (CCL); multiple myeloma (MM); Hodgkin lymphoma (HL), including all classical Hodgkin lymphoma cell types; all non-Hodgkin's lymphomas (NHL); cancerous histiocytic disorders; and mastocytosis.

10. The method according to claim 1, wherein the cancer cell marker is MUM1.

11. The method according to claim 1, wherein the cancer cell marker is PAX5.

12. The method according to claim 1, wherein the cancer cell marker is bcl-6.

13. The method according to claim 1, wherein the cancer cell marker is TdT.

14. The method according to claim 1, wherein the cell cycle marker is pS-Rb protein having a phosphorylated serine residue selected from the group consisting of serine 608, serine 780, serine 795, and serine 807/811.

15. A method of detecting proliferating cancerous cells in a lymphoid or bone marrow tissue sample by performing the method according to claim 1, wherein the first primary antibody or antigen-binding fragment thereof binds to a nuclear marker protein for a cancer cell and the second primary antibody or antigen-binding fragment thereof binds to a nuclear cell cycle marker protein, and proliferating cancerous cells are identified by the presence of a nucleus stained by both pigments.

16. The method of claim 15, further comprising:
determining the cancerous stage of the lymphoid or bone marrow tissue sample by comparing the number of cancer cells that have entered cell cycle and are proliferating versus the total number of cancer cells.

17. The method according to claim 15, wherein the cancer cell is selected from the group of acute myelogenous leukemias (AML); acute promyelocytic leukemia (APL); myeloproliferative disorders (MPD), including chronic myelogenous leukemia (CML) and polycythemia vera; all myelodysplastic syndromes (MDS) and myelodysplastic/myeloproliferative diseases; all acute lymphoblastic leukemias (ALL), including precursor B-lymphoblastic leukemia/lymphoma and precursor T lymphoblastic leukemia/lymphoma; chronic lymphocytic leukemia (CCL); multiple myeloma (MM); Hodgkin lymphoma (HL), including all classical Hodgkin lymphoma cell types; all non-Hodgkin's lymphomas (NHL); cancerous histiocytic disorders; and mastocytosis.

18. The method according to claim 15, wherein the bone marrow tissue sample is from a bone marrow biopsy.

19. A method of assessing the cancer status and progression in a tissue sample comprising:
performing the method according to claim 8 on at least two occasions with a time delay between the at least two occasions; and
determining whether there exists, following the time delay, an increase in the percentage of cells in the patient sample that are identified during said identifying step, wherein the increase indicates a resurgence or progression of cancer condition.

20. A method of assessing the efficacy of cancer therapy by performing the method of claim 8 on first and second patient samples obtained from a cancerous lymphoid or cancerous bone marrow tissue of a patient before and after, respectively, providing cancer therapy to the patient, wherein a change in the percentage of identified cells indicates the efficacy of the cancer therapy.

21. The method according to claim 1, wherein the provided tissue sample is a lymphoid tissue sample.

22. The method according to claim 21, wherein the lymphoid tissue sample is obtained from tonsil, lymph node, spleen, or thymus.

23. The method according to claim 1, wherein the provided tissue sample is a bone marrow tissue sample.

24. The method according to claim 1, wherein the provided lymphoid or bone marrow tissue sample is not exposed to a counterstain.

25. A method for discriminating MUM1+/Ki67+ multiple myeloma cells during immunohistochemistry analysis of tissue samples containing heterogeneous populations of cells, said method consisting essentially of:
providing a fixed, paraffin-embedded histological lymphoid or bone marrow tissue sample;
exposing the provided lymphoid or bone marrow tissue sample to first and second primary antibodies, or antigen-binding fragments thereof comprising all complementarity determining regions of the respective primary antibody, that recognize, respectively, MUM1 and Ki67, thereby forming an antibody-labeled sample;
exposing the antibody-labeled sample to first and second secondary antibodies, or antigen-binding fragments thereof comprising all complementarity determining regions of the respective secondary antibody, the first secondary antibody, or antigen-binding fragment thereof, binding to the first primary antibody, or antigen-binding fragment thereof, and the second secondary antibody, or antigen-binding fragment thereof, binding to the second primary antibody, or antigen-binding fragment thereof, the first and second secondary antibodies, or antigen-binding fragments thereof, each comprising a reagent for forming distinct pigments;
exposing the resulting sample to one or more chromogenic substrates for the reagents of the first and second secondary antibodies, or antigen-binding fragments thereof, thereby forming one pigment in nuclei containing MUM1 and another pigment in nuclei containing Ki67, or both pigments in nuclei containing both MUM1 and Ki67; and
using light microscopy, distinguishing MUM1+/Ki67+ proliferating multiple myeloma cells by the different coloration of nuclei labeled by both pigments from MUM1+/Ki67− non-proliferating multiple myeloma cells having nuclei labeled by said one pigment and MUM1−/Ki67+ proliferating non-multiple myeloma cells having nuclei labeled by said another pigment, wherein the nuclei are further identified by one or more of size, shape, and aspect ratio.

* * * * *